(12) United States Patent
Mannanal

(10) Patent No.: US 12,369,948 B2
(45) Date of Patent: *Jul. 29, 2025

(54) STRUT ATTACHMENTS FOR EXTERNAL FIXATION FRAME

(71) Applicant: Stryker European Operations Holdings LLC, Kalamazoo, MI (US)

(72) Inventor: Subash K. Mannanal, Boonton, NJ (US)

(73) Assignee: Stryker European Operations Holdings LLC, Portage, MI (US)

( * ) Notice: Subject to any disclaimer, the term of this patent is extended or adjusted under 35 U.S.C. 154(b) by 160 days.

This patent is subject to a terminal disclaimer.

(21) Appl. No.: 18/216,665

(22) Filed: Jun. 30, 2023

(65) Prior Publication Data

US 2023/0338061 A1    Oct. 26, 2023

Related U.S. Application Data

(63) Continuation of application No. 17/112,398, filed on Dec. 4, 2020, now Pat. No. 11,723,690, which is a continuation of application No. 15/419,596, filed on Jan. 30, 2017, now Pat. No. 10,874,433.

(51) Int. Cl.
*A61B 17/62* (2006.01)
*A61B 17/66* (2006.01)

(52) U.S. Cl.
CPC .............. *A61B 17/62* (2013.01); *A61B 17/66* (2013.01)

(58) Field of Classification Search
CPC ................................................ A61B 17/60–66
See application file for complete search history.

(56) References Cited

U.S. PATENT DOCUMENTS

| 1,899,555 | A | 2/1933 | Campbell |
| 2,055,024 | A | 9/1936 | Bittner |
| 2,250,417 | A | 7/1941 | Ettinger |
| 2,333,033 | A | 10/1943 | Mraz |
| 2,391,537 | A | 12/1945 | Anderson |

(Continued)

FOREIGN PATENT DOCUMENTS

| DE | 3439795 A1 | 6/1985 |
| DE | 3729253 A1 | 3/1989 |

(Continued)

OTHER PUBLICATIONS

European Search Report, including Written Opinion, for EP Application No. 18153883.6, dated May 25, 2018.

*Primary Examiner* — Julianna N Harvey
(74) *Attorney, Agent, or Firm* — SLEMAN & LUND LLP

(57) ABSTRACT

Disclosed herein are strut attachments for external fixation frames. The strut attachments provide solutions for frame configurations in which it is not possible to attach a strut at its ends to corresponding rings. The strut attachments may be considered an outrigger type of mechanism that achieves more travel out of completely collapsed struts. The strut attachments, each having a pivot and a hinge joint, allow a strut to be attached on the level of a first ring and extend at least partially proximally or distally to a second ring depending on the frame of reference of the ring system. These strut attachments may be used when the fully collapsed length of the strut will not allow the rings to get any closer to one another than is needed or proscribed. In such cases, the strut attachments allow for even tighter ring to ring distance.

13 Claims, 13 Drawing Sheets

(56) References Cited

U.S. PATENT DOCUMENTS

| | | |
|---|---|---|
| 2,393,831 A | 1/1946 | Stader |
| 2,406,987 A | 9/1946 | Anderson |
| 2,432,695 A | 12/1947 | Speas |
| 3,727,610 A | 4/1973 | Riniker |
| 3,866,607 A | 2/1975 | Forsythe et al. |
| 3,941,123 A | 3/1976 | Volkov et al. |
| 3,975,032 A | 8/1976 | Bent et al. |
| 3,977,397 A | 8/1976 | Kalnberz et al. |
| 3,985,127 A | 10/1976 | Volkov et al. |
| 4,006,740 A | 2/1977 | Volkov et al. |
| 4,033,340 A | 7/1977 | Kalnberz |
| 4,091,880 A | 5/1978 | Troutner et al. |
| 4,100,919 A | 7/1978 | Oganesyan et al. |
| 4,112,935 A | 9/1978 | Latypov et al. |
| 4,308,863 A | 1/1982 | Fischer |
| 4,312,336 A | 1/1982 | Danieletto et al. |
| 4,338,927 A | 7/1982 | Volkov et al. |
| 4,365,624 A | 12/1982 | Jaquet |
| 4,450,834 A | 5/1984 | Fischer |
| 4,482,264 A | 11/1984 | Kodera |
| 4,488,542 A | 12/1984 | Helland |
| RE31,809 E | 1/1985 | Danieletto et al. |
| 4,535,763 A | 8/1985 | Jaquet |
| 4,570,625 A | 2/1986 | Harris et al. |
| 4,604,997 A | 8/1986 | De Bastiani et al. |
| 4,607,625 A | 8/1986 | Schenck |
| 4,615,338 A | 10/1986 | Ilizarov et al. |
| 4,621,627 A | 11/1986 | DeBastiani et al. |
| 4,624,249 A | 11/1986 | Alvarez Cambras |
| 4,669,907 A | 6/1987 | Patton |
| 4,768,524 A | 9/1988 | Hardy |
| 4,784,125 A | 11/1988 | Monticelli et al. |
| 4,828,277 A | 5/1989 | De Bastiani et al. |
| 4,862,172 A | 8/1989 | Ross |
| 4,889,111 A | 12/1989 | Ben-Dov |
| 4,890,631 A | 1/1990 | Hardy |
| 4,923,458 A | 5/1990 | Fischer |
| 4,936,843 A | 6/1990 | Sohngen |
| 4,946,179 A | 8/1990 | De Bastiani et al. |
| 4,964,320 A | 10/1990 | Lee, Jr. |
| 4,973,331 A | 11/1990 | Pursley et al. |
| 4,978,347 A | 12/1990 | Ilizarov |
| 4,988,349 A | 1/1991 | Pennig |
| 5,019,077 A | 5/1991 | De Bastiani et al. |
| 5,026,374 A | 6/1991 | Dezza et al. |
| 5,028,180 A | 7/1991 | Sheldon et al. |
| 5,062,844 A | 11/1991 | Jamison et al. |
| 5,067,954 A | 11/1991 | Ilizarov |
| 5,087,258 A | 2/1992 | Schewior |
| 5,102,411 A | 4/1992 | Hotchkiss et al. |
| 5,108,394 A | 4/1992 | Kurokawa et al. |
| 5,129,898 A | 7/1992 | Brusasco |
| 5,156,605 A | 10/1992 | Pursley et al. |
| 5,180,380 A | 1/1993 | Pursley et al. |
| 5,207,676 A | 5/1993 | Canadell et al. |
| 5,275,598 A | 1/1994 | Cook |
| 5,281,224 A | 1/1994 | Faccioli et al. |
| 5,292,322 A | 3/1994 | Faccioli et al. |
| 5,312,410 A | 5/1994 | Miller et al. |
| 5,314,426 A | 5/1994 | Pohl et al. |
| 5,320,622 A | 6/1994 | Faccioli et al. |
| 5,320,623 A | 6/1994 | Pennig |
| 5,334,202 A | 8/1994 | Carter |
| 5,342,360 A | 8/1994 | Faccioli et al. |
| 5,376,090 A | 12/1994 | Pennig |
| RE34,985 E | 6/1995 | Pennig |
| 5,431,659 A | 7/1995 | Ross, Jr. et al. |
| 5,433,720 A | 7/1995 | Faccioli et al. |
| 5,437,668 A | 8/1995 | Aronson et al. |
| 5,443,464 A | 8/1995 | Russell et al. |
| 5,451,225 A | 9/1995 | Ross, Jr. et al. |
| 5,496,319 A | 3/1996 | Allard et al. |
| 5,540,686 A | 7/1996 | Zippel et al. |
| 5,601,551 A | 2/1997 | Taylor et al. |
| 5,620,449 A | 4/1997 | Faccioli et al. |
| 5,630,814 A | 5/1997 | Ross, Jr. et al. |
| 5,643,319 A | 7/1997 | Green et al. |
| 5,649,927 A | 7/1997 | Kilpela et al. |
| 5,662,648 A | 9/1997 | Faccioli et al. |
| 5,676,664 A | 10/1997 | Allard et al. |
| 5,681,309 A | 10/1997 | Ross, Jr. et al. |
| 5,681,318 A | 10/1997 | Pennig et al. |
| 5,688,271 A | 11/1997 | Faccioli et al. |
| 5,700,263 A | 12/1997 | Schendel |
| 5,702,389 A | 12/1997 | Taylor et al. |
| 5,707,370 A | 1/1998 | Berki et al. |
| 5,725,526 A | 3/1998 | Allard et al. |
| 5,728,095 A | 3/1998 | Taylor et al. |
| 5,728,096 A | 3/1998 | Faccioli et al. |
| 5,741,252 A | 4/1998 | Mazzio et al. |
| 5,746,741 A | 5/1998 | Kraus et al. |
| 5,766,173 A | 6/1998 | Ross, Jr. et al. |
| 5,766,179 A | 6/1998 | Faccioli et al. |
| 5,776,132 A | 7/1998 | Blyakher |
| 5,788,695 A | 8/1998 | Richardson |
| 5,797,908 A | 8/1998 | Meyers et al. |
| 5,827,282 A | 10/1998 | Pennig |
| 5,843,081 A | 12/1998 | Richardson |
| 5,863,292 A | 1/1999 | Tosic |
| 5,870,834 A | 2/1999 | Sheldon |
| 5,881,878 A | 3/1999 | Faccioli et al. |
| 5,885,282 A | 3/1999 | Szabo |
| 5,891,143 A | 4/1999 | Taylor et al. |
| 5,902,302 A | 5/1999 | Berki et al. |
| 5,902,306 A | 5/1999 | Norman |
| 5,919,192 A | 7/1999 | Shouts |
| 5,921,985 A | 7/1999 | Ross, Jr. et al. |
| 5,928,230 A | 7/1999 | Tosic |
| 5,928,234 A | 7/1999 | Manspeizer |
| 5,931,837 A | 8/1999 | Marsh et al. |
| 5,951,556 A | 9/1999 | Faccioli et al. |
| 5,968,043 A | 10/1999 | Ross, Jr. et al. |
| 5,971,984 A | 10/1999 | Taylor et al. |
| 5,976,133 A | 11/1999 | Kraus et al. |
| 5,976,136 A | 11/1999 | Bailey et al. |
| 5,997,537 A | 12/1999 | Walulik |
| 6,015,413 A | 1/2000 | Faccioli et al. |
| 6,017,341 A | 1/2000 | Windhagen et al. |
| 6,021,579 A | 2/2000 | Schimmels et al. |
| 6,024,745 A | 2/2000 | Faccioli et al. |
| 6,027,506 A | 2/2000 | Faccioli et al. |
| 6,030,386 A | 2/2000 | Taylor et al. |
| 6,033,412 A | 3/2000 | Losken et al. |
| 6,036,691 A | 3/2000 | Richardson |
| 6,042,585 A | 3/2000 | Norman |
| 6,102,911 A | 8/2000 | Faccioli et al. |
| 6,106,525 A | 8/2000 | Sachse |
| 6,126,661 A | 10/2000 | Faccioli et al. |
| 6,129,727 A | 10/2000 | Austin et al. |
| 6,143,012 A | 11/2000 | Gausepohl |
| 6,235,029 B1 | 5/2001 | Faccioli et al. |
| 6,245,071 B1 | 6/2001 | Pierson |
| 6,277,118 B1 | 8/2001 | Grant et al. |
| 6,328,737 B1 | 12/2001 | Moorcroft et al. |
| 6,340,361 B1 | 1/2002 | Kraus et al. |
| 6,342,054 B1 | 1/2002 | Mata |
| 6,355,037 B1 | 3/2002 | Crosslin et al. |
| 6,357,954 B1 | 3/2002 | Timoney |
| 6,364,824 B1 | 4/2002 | Fitzsimmons |
| 6,461,358 B1 | 10/2002 | Faccioli et al. |
| 6,485,523 B2 | 11/2002 | Pierce et al. |
| 6,500,177 B1 | 12/2002 | Martinelli et al. |
| 6,537,274 B1 | 3/2003 | Katz |
| 6,537,275 B2 | 3/2003 | Venturini et al. |
| 6,582,473 B2 | 6/2003 | Pierce et al. |
| 6,616,664 B2 | 9/2003 | Walulik et al. |
| 6,642,370 B1 | 11/2003 | Wise |
| 6,652,524 B1 | 11/2003 | Weiner |
| 6,689,140 B2 | 2/2004 | Cohen |
| 6,699,251 B1 | 3/2004 | Venturini |
| 6,701,174 B1 | 3/2004 | Krause et al. |
| 6,702,814 B2 | 3/2004 | Walulik et al. |
| 6,716,212 B1 | 4/2004 | Pickens |
| 6,722,368 B1 | 4/2004 | Shaikh |

(56) References Cited

U.S. PATENT DOCUMENTS

| | | |
|---|---|---|
| 6,736,775 B2 | 5/2004 | Phillips |
| 6,746,448 B2 | 6/2004 | Weiner et al. |
| 6,749,611 B2 | 6/2004 | Venturini et al. |
| 6,793,655 B2 | 9/2004 | Orsak |
| 6,840,939 B2 | 1/2005 | Venturini et al. |
| 6,860,883 B2 | 3/2005 | Janowski et al. |
| 6,949,100 B1 | 9/2005 | Venturini |
| 6,964,663 B2 | 11/2005 | Grant et al. |
| D518,174 S | 3/2006 | Venturini et al. |
| 7,048,735 B2 | 5/2006 | Ferrante et al. |
| 7,094,240 B2 | 8/2006 | Molz, IV et al. |
| 7,108,641 B2 | 9/2006 | Pertegaz-Esteban |
| 7,144,378 B2 | 12/2006 | Arnott |
| 7,147,639 B2 | 12/2006 | Berki et al. |
| 7,147,640 B2 | 12/2006 | Huebner et al. |
| 7,226,449 B2 | 6/2007 | Venturini et al. |
| 7,241,074 B2 | 7/2007 | Thomke et al. |
| 7,261,713 B2 | 8/2007 | Langmaid et al. |
| 7,282,052 B2 | 10/2007 | Mullaney |
| 7,291,148 B2 | 11/2007 | Agee et al. |
| 7,306,601 B2 | 12/2007 | McGrath et al. |
| 7,311,711 B2 | 12/2007 | Cole |
| 7,361,176 B2 | 4/2008 | Cooper et al. |
| 7,388,972 B2 | 6/2008 | Kitson |
| 7,422,593 B2 | 9/2008 | Cresina et al. |
| 7,449,023 B2 | 11/2008 | Walulik et al. |
| 7,468,063 B2 | 12/2008 | Walulik et al. |
| 7,479,142 B2 | 1/2009 | Weiner et al. |
| 7,491,008 B2 | 2/2009 | Thomke et al. |
| 7,575,575 B2 | 8/2009 | Olsen et al. |
| 7,578,822 B2 | 8/2009 | Rezach et al. |
| RE40,914 E | 9/2009 | Taylor et al. |
| 7,608,074 B2 | 10/2009 | Austin et al. |
| 7,632,271 B2 | 12/2009 | Baumgartner et al. |
| 7,645,279 B1 | 1/2010 | Haupt |
| 7,655,403 B2 | 2/2010 | Wise |
| 7,670,340 B2 | 3/2010 | Brivio et al. |
| 7,699,848 B2 | 4/2010 | Hoffman et al. |
| 7,708,736 B2 | 5/2010 | Mullaney |
| 7,708,737 B2 | 5/2010 | Kraft et al. |
| 7,722,651 B2 | 5/2010 | Kwak et al. |
| 7,749,224 B2 | 7/2010 | Cresina et al. |
| 7,763,020 B2 | 7/2010 | Draper |
| 7,769,488 B2 | 8/2010 | Curtis |
| 7,776,046 B2 | 8/2010 | Boyd et al. |
| 7,806,843 B2 | 10/2010 | Marin |
| 7,815,586 B2 | 10/2010 | Grant et al. |
| 7,833,254 B2 | 11/2010 | Celli et al. |
| 7,875,030 B2 | 1/2011 | Hoffmann-Clair et al. |
| 7,881,771 B2 | 2/2011 | Koo et al. |
| 7,887,498 B2 | 2/2011 | Marin |
| 7,931,650 B2 | 4/2011 | Winquist et al. |
| 7,935,115 B2 | 5/2011 | Hagert |
| 7,938,829 B2 | 5/2011 | Mullaney |
| 7,955,333 B2 | 6/2011 | Yeager |
| 7,955,334 B2 | 6/2011 | Steiner et al. |
| 7,985,221 B2 | 7/2011 | Coull et al. |
| 8,002,773 B2 | 8/2011 | Kehres et al. |
| 8,020,753 B2 | 9/2011 | Wheeler et al. |
| 8,029,505 B2 | 10/2011 | Hearn et al. |
| 8,055,487 B2 | 11/2011 | James |
| 8,057,474 B2 | 11/2011 | Knuchel et al. |
| 8,062,293 B2 | 11/2011 | Steiner et al. |
| 8,096,998 B2 | 1/2012 | Cresina |
| 8,114,077 B2 | 2/2012 | Steiner et al. |
| 8,123,747 B2 | 2/2012 | Hajianpour |
| 8,137,347 B2 | 3/2012 | Weiner et al. |
| 8,142,432 B2 | 3/2012 | Matityahu |
| 8,147,490 B2 | 4/2012 | Bauer |
| 8,147,491 B2 | 4/2012 | Lavi |
| 8,157,800 B2 | 4/2012 | Vvedensky et al. |
| 8,162,942 B2 | 4/2012 | Coati et al. |
| 8,167,880 B2 | 5/2012 | Vasta |
| 8,170,719 B2 | 5/2012 | Tsusaka et al. |
| 8,172,849 B2 | 5/2012 | Noon et al. |
| 8,175,749 B2 | 5/2012 | Tsusaka et al. |
| 8,182,483 B2 | 5/2012 | Bagnasco et al. |
| 8,187,274 B2 | 5/2012 | Schulze |
| 8,192,434 B2 | 6/2012 | Huebner et al. |
| 8,202,273 B2 | 6/2012 | Karidis |
| 8,251,937 B2 | 8/2012 | Marin |
| 8,257,353 B2 | 9/2012 | Wong et al. |
| 8,282,652 B2 | 10/2012 | Mackenzi et al. |
| 8,323,282 B2 | 12/2012 | Taylor |
| 8,333,766 B2 | 12/2012 | Edelhauser et al. |
| 8,337,534 B2 | 12/2012 | Celli et al. |
| 8,377,060 B2 | 2/2013 | Vasta et al. |
| 8,382,760 B2 | 2/2013 | Mantovani et al. |
| 8,388,619 B2 | 3/2013 | Mullaney |
| 8,388,625 B2 | 3/2013 | Bagnasco et al. |
| 8,419,732 B2 | 4/2013 | Mullaney |
| 8,419,750 B2 | 4/2013 | Kienzle, III et al. |
| 8,425,512 B2 | 4/2013 | Vasta et al. |
| 8,425,519 B2 | 4/2013 | Mast et al. |
| 8,425,521 B2 | 4/2013 | Cremer et al. |
| 8,430,878 B2 | 4/2013 | Vasta et al. |
| 8,439,914 B2 | 5/2013 | Ross et al. |
| 8,439,916 B2 | 5/2013 | Coati et al. |
| 8,444,644 B2 | 5/2013 | Ross et al. |
| 8,454,604 B2 | 6/2013 | Wong et al. |
| 8,460,293 B2 | 6/2013 | Coati et al. |
| 8,469,958 B2 | 6/2013 | Stevens |
| 8,469,966 B2 | 6/2013 | Allen et al. |
| 8,506,566 B2 | 8/2013 | Karidis et al. |
| 8,523,858 B2 | 9/2013 | Lessig et al. |
| 8,540,713 B2 | 9/2013 | Zandona et al. |
| 8,574,232 B1 | 11/2013 | Ross et al. |
| 8,608,740 B2 | 12/2013 | Butikofer et al. |
| 8,623,061 B2 | 1/2014 | Quevedo et al. |
| 8,654,150 B2 | 2/2014 | Haskell |
| 8,679,116 B2 | 3/2014 | Cheng et al. |
| 8,679,117 B2 | 3/2014 | Knuchel et al. |
| 8,702,705 B2 | 4/2014 | Ziran et al. |
| 8,721,641 B2 | 5/2014 | Ottoboni et al. |
| 8,728,079 B2 | 5/2014 | Zandona et al. |
| 8,764,750 B2 | 7/2014 | Zgonis et al. |
| 8,834,467 B2 | 9/2014 | Singh et al. |
| 8,852,252 B2 | 10/2014 | Venturini et al. |
| 8,864,750 B2 | 10/2014 | Ross et al. |
| 8,864,763 B2 | 10/2014 | Murray et al. |
| 8,870,868 B2 | 10/2014 | Clifford et al. |
| 8,888,777 B2 | 11/2014 | Mullaney |
| 8,915,914 B2 | 12/2014 | Venturini et al. |
| 8,951,253 B2 | 2/2015 | Bagnasco et al. |
| 9,039,706 B2 | 5/2015 | Murray et al. |
| 9,050,141 B2 | 6/2015 | Zhang et al. |
| 9,078,700 B2 | 7/2015 | Ross et al. |
| 9,084,632 B2 | 7/2015 | Orsak et al. |
| 9,155,559 B2 | 10/2015 | Ross et al. |
| RE45,888 E | 2/2016 | Bagnasco et al. |
| 9,289,238 B2 | 3/2016 | Ross et al. |
| 9,295,493 B2 | 3/2016 | Ross et al. |
| 9,308,025 B2 | 4/2016 | Zgonis et al. |
| RE46,077 E | 7/2016 | Bagnasco et al. |
| 9,381,042 B2 | 7/2016 | Ross et al. |
| 9,443,302 B2 | 9/2016 | Vvedenskiy et al. |
| 9,445,841 B2 | 9/2016 | Samchukov et al. |
| 9,456,849 B2 | 10/2016 | Ross et al. |
| 2001/0049525 A1 | 12/2001 | Slocum |
| 2001/0049526 A1 | 12/2001 | Venturini et al. |
| 2002/0010465 A1 | 1/2002 | Koo et al. |
| 2002/0013584 A1 | 1/2002 | Termaten |
| 2002/0042613 A1 | 4/2002 | Mata |
| 2002/0072753 A1 | 6/2002 | Cohen |
| 2002/0165543 A1 | 11/2002 | Winquist et al. |
| 2003/0069580 A1 | 4/2003 | Langmaid et al. |
| 2003/0109879 A1 | 6/2003 | Orsak |
| 2003/0114852 A1 | 6/2003 | Biedermann et al. |
| 2003/0149429 A1 | 8/2003 | Ferrante et al. |
| 2003/0149430 A1 | 8/2003 | Ferrante et al. |
| 2003/0153910 A1 | 8/2003 | Janowski et al. |
| 2003/0181911 A1 | 9/2003 | Venturini |
| 2003/0191466 A1 | 10/2003 | Austin et al. |
| 2003/0216734 A1 | 11/2003 | Mingozzi et al. |

(56) References Cited

U.S. PATENT DOCUMENTS

| | | |
|---|---|---|
| 2003/0225405 A1 | 12/2003 | Weiner |
| 2003/0225406 A1 | 12/2003 | Weiner et al. |
| 2004/0059331 A1 | 3/2004 | Mullaney |
| 2004/0068187 A1 | 4/2004 | Krause et al. |
| 2004/0073211 A1 | 4/2004 | Austin et al. |
| 2004/0073212 A1 | 4/2004 | Kim |
| 2004/0097922 A1 | 5/2004 | Mullaney |
| 2004/0097944 A1 | 5/2004 | Koman et al. |
| 2004/0116926 A1 | 6/2004 | Venturini et al. |
| 2004/0167518 A1 | 8/2004 | Estrada |
| 2004/0230191 A1 | 11/2004 | Frey et al. |
| 2004/0249375 A1 | 12/2004 | Agee et al. |
| 2005/0015087 A1 | 1/2005 | Walulik et al. |
| 2005/0043730 A1 | 2/2005 | Janowski et al. |
| 2005/0043731 A1 | 2/2005 | Labbe et al. |
| 2005/0059968 A1 | 3/2005 | Grant et al. |
| 2005/0085810 A1 | 4/2005 | Lutz et al. |
| 2005/0113829 A1 | 5/2005 | Nalulik et al. |
| 2005/0119656 A1 | 6/2005 | Ferrante et al. |
| 2005/0149018 A1 | 7/2005 | Cooper et al. |
| 2005/0149086 A1 | 7/2005 | Huxel et al. |
| 2005/0165394 A1 | 7/2005 | Boyce et al. |
| 2005/0215997 A1 | 9/2005 | Austin et al. |
| 2005/0261680 A1 | 11/2005 | Draper |
| 2006/0069392 A1 | 3/2006 | Renzi Brivio et al. |
| 2006/0155276 A1 | 7/2006 | Walulik et al. |
| 2006/0184169 A1 | 8/2006 | Stevens |
| 2006/0229602 A1 | 10/2006 | Olsen |
| 2006/0229605 A1 | 10/2006 | Olsen |
| 2006/0235402 A1 | 10/2006 | Celli et al. |
| 2006/0276786 A1 | 12/2006 | Brinker |
| 2006/0287652 A1 | 12/2006 | Lessig et al. |
| 2007/0038217 A1 | 2/2007 | Brown et al. |
| 2007/0043354 A1 | 2/2007 | Koo et al. |
| 2007/0049930 A1 | 3/2007 | Hearn et al. |
| 2007/0055234 A1 | 3/2007 | McGrath et al. |
| 2007/0100358 A2 | 5/2007 | Romero-Ortega et al. |
| 2007/0161983 A1 | 7/2007 | Cresina et al. |
| 2007/0161984 A1 | 7/2007 | Cresina et al. |
| 2007/0225704 A1 | 9/2007 | Ziran et al. |
| 2007/0282338 A1 | 12/2007 | Mullaney |
| 2008/0021451 A1 | 1/2008 | Coull et al. |
| 2008/0051779 A1 | 2/2008 | Mackenzie et al. |
| 2008/0131877 A1 | 6/2008 | Wise |
| 2008/0228185 A1 | 9/2008 | Vasta et al. |
| 2008/0234554 A1 | 9/2008 | Vvedensky et al. |
| 2008/0262495 A1 | 10/2008 | Coati et al. |
| 2008/0269741 A1 | 10/2008 | Karidis |
| 2008/0269810 A1 | 10/2008 | Zhang et al. |
| 2008/0281332 A1 | 11/2008 | Taylor |
| 2008/0300691 A1 | 12/2008 | Romero-Ortega et al. |
| 2009/0018541 A1 | 1/2009 | Lavi |
| 2009/0036890 A1 | 2/2009 | Karidis |
| 2009/0036891 A1 | 2/2009 | Brown et al. |
| 2009/0036892 A1 | 2/2009 | Karidis et al. |
| 2009/0082776 A1 | 3/2009 | Cresina |
| 2009/0088751 A1 | 4/2009 | Mullaney |
| 2009/0105621 A1 | 4/2009 | Boyd et al. |
| 2009/0131935 A1 | 5/2009 | Yeager |
| 2009/0177197 A1 | 7/2009 | Marin |
| 2009/0177198 A1 | 7/2009 | Theodoros et al. |
| 2009/0198235 A1 | 8/2009 | Steiner et al. |
| 2009/0198273 A1 | 8/2009 | Zhang et al. |
| 2009/0198279 A1 | 8/2009 | Zhang et al. |
| 2009/0264882 A1 | 10/2009 | Steiner et al. |
| 2009/0264883 A1 | 10/2009 | Steiner et al. |
| 2009/0275944 A1 | 11/2009 | Huebner et al. |
| 2009/0287212 A1 | 11/2009 | Hirata et al. |
| 2009/0292285 A1 | 11/2009 | Salzhauer |
| 2009/0312757 A1 | 12/2009 | Kehres et al. |
| 2009/0326532 A1 | 12/2009 | Schulze |
| 2010/0057127 A1 | 3/2010 | McGuire et al. |
| 2010/0087819 A1 | 4/2010 | Mullaney |
| 2010/0087820 A1 | 4/2010 | Mantovani et al. |
| 2010/0114103 A1 | 5/2010 | Harrison et al. |
| 2010/0125273 A1 | 5/2010 | Schwieger et al. |
| 2010/0131012 A1 | 5/2010 | Ralph et al. |
| 2010/0143928 A1 | 6/2010 | Wise |
| 2010/0145336 A1 | 6/2010 | Draper |
| 2010/0179548 A1 | 7/2010 | Marin |
| 2010/0191239 A1 | 7/2010 | Sakkers et al. |
| 2010/0222778 A1 | 9/2010 | Bagnasco et al. |
| 2010/0234844 A1 | 9/2010 | Edelhauser et al. |
| 2010/0234845 A1 | 9/2010 | Mullaney |
| 2010/0249779 A1 | 9/2010 | Hotchkiss et al. |
| 2010/0249853 A1 | 9/2010 | Celli et al. |
| 2010/0280516 A1 | 11/2010 | Taylor |
| 2010/0286826 A1 | 11/2010 | Tsusaka et al. |
| 2010/0298827 A1 | 11/2010 | Cremer et al. |
| 2010/0305568 A1 | 12/2010 | Ross et al. |
| 2010/0312243 A1 | 12/2010 | Ross et al. |
| 2010/0318084 A1 | 12/2010 | Hajianpour |
| 2010/0331840 A1 | 12/2010 | Ross et al. |
| 2011/0004199 A1 | 1/2011 | Ross et al. |
| 2011/0060336 A1 | 3/2011 | Pool et al. |
| 2011/0066151 A1 | 3/2011 | Murner et al. |
| 2011/0082458 A1 | 4/2011 | Crozet et al. |
| 2011/0103676 A1 | 5/2011 | Mullaney |
| 2011/0112533 A1 | 5/2011 | Venturini et al. |
| 2011/0118737 A1 | 5/2011 | Vasta et al. |
| 2011/0118738 A1 | 5/2011 | Vasta et al. |
| 2011/0125196 A1 | 5/2011 | Quevedo et al. |
| 2011/0137312 A1 | 6/2011 | Mantovani et al. |
| 2011/0172663 A1 | 7/2011 | Mullaney |
| 2011/0172664 A1 | 7/2011 | Bagnasco et al. |
| 2011/0178638 A1 | 7/2011 | Tsusaka et al. |
| 2011/0196380 A1 | 8/2011 | Cremer et al. |
| 2011/0208186 A1 | 8/2011 | Marin |
| 2011/0208187 A1 | 8/2011 | Wong et al. |
| 2011/0245830 A1 | 10/2011 | Zgonis et al. |
| 2011/0245882 A1 | 10/2011 | Venturini et al. |
| 2011/0288549 A1 | 11/2011 | Steiner et al. |
| 2011/0313418 A1 | 12/2011 | Nikonovas |
| 2011/0313419 A1 | 12/2011 | Mullaney |
| 2012/0004659 A1 | 1/2012 | Miller et al. |
| 2012/0029516 A1 | 2/2012 | Taylor |
| 2012/0041439 A1 | 2/2012 | Singh et al. |
| 2012/0078251 A1 | 3/2012 | Benenati et al. |
| 2012/0089142 A1 | 4/2012 | Mullaney et al. |
| 2012/0095462 A1 | 4/2012 | Miller |
| 2012/0136355 A1 | 5/2012 | Wolfson |
| 2012/0143190 A1 | 6/2012 | Wolfson |
| 2012/0172875 A1 | 7/2012 | Coati et al. |
| 2012/0172876 A1 | 7/2012 | Coati et al. |
| 2012/0184958 A1 | 7/2012 | Knuchel et al. |
| 2012/0209264 A1 | 8/2012 | Zandona et al. |
| 2012/0209266 A1 | 8/2012 | Ottoboni et al. |
| 2012/0215222 A1 | 8/2012 | Yapp et al. |
| 2012/0221057 A1 | 8/2012 | Zhang et al. |
| 2012/0232554 A1 | 9/2012 | Shaevitz et al. |
| 2012/0277744 A1 | 11/2012 | Lindahl et al. |
| 2012/0303028 A1 | 11/2012 | Wong et al. |
| 2012/0303029 A1 | 11/2012 | Vasta et al. |
| 2013/0090691 A1 | 4/2013 | Zhang et al. |
| 2013/0123784 A1 | 5/2013 | Ross et al. |
| 2013/0131675 A1 | 5/2013 | Vasta et al. |
| 2013/0131676 A1 | 5/2013 | Mullaney |
| 2013/0215114 A1 | 8/2013 | Cherkashin et al. |
| 2013/0245625 A1 | 9/2013 | Vasta et al. |
| 2013/0253511 A1 | 9/2013 | Cheng et al. |
| 2013/0253513 A1 | 9/2013 | Ross et al. |
| 2013/0289575 A1 | 10/2013 | Edelhauser et al. |
| 2014/0025077 A1 | 1/2014 | Zandona et al. |
| 2014/0046326 A1 | 2/2014 | Wong |
| 2014/0058389 A1 | 2/2014 | Singh et al. |
| 2014/0066931 A1 | 3/2014 | Myers et al. |
| 2014/0094857 A1 | 4/2014 | Quevedo et al. |
| 2014/0128868 A1 | 5/2014 | Harrison et al. |
| 2014/0135764 A1 | 5/2014 | Ross et al. |
| 2014/0243825 A1 | 8/2014 | Yapp et al. |
| 2014/0276817 A1 | 9/2014 | Murray et al. |
| 2014/0276819 A1 | 9/2014 | Cresina et al. |
| 2014/0276820 A1 | 9/2014 | Cresina et al. |
| 2014/0276821 A1 | 9/2014 | Murray et al. |

(56) References Cited

U.S. PATENT DOCUMENTS

| | | |
|---|---|---|
| 2014/0276822 A1 | 9/2014 | Cresina et al. |
| 2014/0379038 A1 | 12/2014 | Dogramadzi et al. |
| 2015/0100057 A1 | 4/2015 | Zgonis et al. |
| 2015/0209081 A1 | 7/2015 | Venturini et al. |
| 2015/0216564 A1 | 8/2015 | Salomone et al. |
| 2015/0223842 A1 | 8/2015 | Murray et al. |
| 2015/0257788 A1 | 9/2015 | Jay et al. |
| 2015/0265313 A1 | 9/2015 | Wong et al. |
| 2015/0272624 A1 | 10/2015 | Singh |
| 2015/0305776 A1 | 10/2015 | Ross et al. |
| 2015/0313641 A1 | 11/2015 | Ross et al. |
| 2016/0000465 A1 | 1/2016 | Ross et al. |
| 2016/0022314 A1 | 1/2016 | Bordeaux et al. |
| 2016/0030085 A1 | 2/2016 | Ross et al. |
| 2016/0042571 A1 | 2/2016 | Mikheev et al. |
| 2016/0066956 A1 | 3/2016 | Siemer et al. |
| 2016/0089194 A1 | 3/2016 | Diaz et al. |
| 2016/0157891 A1 | 6/2016 | Zandona et al. |
| 2016/0157892 A1 | 6/2016 | Zandona' et al. |
| 2016/0166285 A1 | 6/2016 | Samchukov et al. |
| 2016/0192964 A1 | 7/2016 | Lorenzini et al. |
| 2016/0287289 A1 | 10/2016 | Lorenzini et al. |
| 2018/0344354 A1 | 12/2018 | Mullaney |
| 2019/0029727 A1 | 1/2019 | Park et al. |

FOREIGN PATENT DOCUMENTS

| | | |
|---|---|---|
| DE | 3802743 A1 | 8/1989 |
| DE | 3935134 A1 | 4/1991 |
| DE | 102005013617 A1 | 9/2006 |
| EP | 0140786 A2 | 5/1985 |
| EP | 0420430 A1 | 4/1991 |
| EP | 0512792 A1 | 11/1992 |
| EP | 0522242 A1 | 1/1993 |
| EP | 611007 A1 | 8/1994 |
| EP | 2789302 A1 | 10/2014 |
| WO | 8503449 A1 | 8/1985 |
| WO | 8911255 A1 | 11/1989 |
| WO | 9106253 A1 | 5/1991 |
| WO | 9111151 A1 | 8/1991 |
| WO | 9207526 A1 | 5/1992 |
| WO | 9418898 A1 | 9/1994 |
| WO | 1997030650 A1 | 8/1997 |
| WO | 2006100283 A1 | 9/2006 |
| WO | 2012102685 A1 | 8/2012 |
| WO | 2014159824 A2 | 10/2014 |

STRUT ATTACHMENTS FOR EXTERNAL FIXATION FRAME

CROSS-REFERENCES TO RELATED APPLICATIONS

The present application is a continuation of U.S. patent application Ser. No. 17/112,398, filed Dec. 4, 2020, which is a continuation of U.S. patent application Ser. No. 15/419,596, filed on Jan. 30, 2017, which issued as U.S. Pat. No. 10,874,433 on Dec. 29, 2020, the disclosures of which are hereby incorporated herein by reference.

FIELD OF THE INVENTION

The present disclosure relates to systems and components of external fixation frames. More particularly, the present disclosure relates to strut attachments for varying the attachment point of a strut to rings of such frames.

BACKGROUND OF THE INVENTION

Many different types of bone deformities can be corrected using external fixation systems to perform the distraction osteogenesis process. For example, an Ilizarov device or similar external fixation system may be used. Such systems generally use rings also designated as fixation plates connected by threaded rods or struts for manipulation, lengthening, angulation, rotation, and translation of deformities of bones. The position of a threaded rod within a hole of a ring is generally fixed using nuts and washers. Adjustable length or telescopic struts are generally fixed to rings at opposite ends thereof with the length of the struts being adjusted by changing the position of a threaded rod within a cylindrical shaft.

As the struts are manipulated, the rings or fixation plates change positions relative to one another, causing the bones or bone segments attached to the fixation plates to change positions relative to one another, until the bone segments are in a desired position relative to one another. Fixation systems have many areas which may be improved including, for example, the ease and precision with which the fixation system may be adjusted by a user, whether a clinician or a patient.

Telescopic struts are used to reduce/treat fractures and correct deformities over time. Patients correct the deformities by prescribed adjustments of the struts. The lengths of the struts are adjusted over time to change the position and orientation of the two rings with respect to one another, which in turn repositions and reorients the bone fragments, with a goal of correcting the bone deformity. The adjustment of the external fixator generally complies with a predetermined correction plan. The struts are generally assembled in a hexapod platform configuration consisting of six struts and gradually adjusted in length (by hand or via an instrument) to address the indicated deformities. The disengagement of such a strut's quick release mechanism, for example, can free the frame and allow the surgeon to quickly manipulate ring position, simplifying frame assembly and fixation to the deformity. Depending on the type of deformity, a strut may run out of its minimum length when the telescopic lengths of components are completely collapsed. In such cases, it would preferable to have a strut connected to a respective ring about its length rather than at its end.

BRIEF SUMMARY OF THE INVENTION

The present invention provides solutions for frame configurations in which it is not possible to attach each strut at its ends to corresponding rings. The strut attachments of the present invention may be considered an outrigger type of mechanism that achieves more travel out of completely collapsed struts. The present invention uses a special type of strut, that attaches on the level of a first ring and extends at least partially proximally or distally to a second ring depending on the frame of reference of the ring system. The strut attachments may be used when the fully collapsed length of the strut will not allow the rings to get any closer to one another than is needed or proscribed. In such cases, the strut attachments allow for even tighter ring to ring distance.

In another embodiment, instead of having a first end of a first strut located proximally to a top surface of a first ring, the first end of the first strut is located between top and bottom surfaces of the first ring. By having a strut attachment member in the shape of a C-clamp, a pivot point of the strut can consistently be at a center the ring thickness between the top and bottom surfaces thereof.

A first aspect of the present invention is with regard to the strut attachment member coupled to each strut in an external fixation system. Each strut attachment allows for two degrees of freedom between the strut and a respective ring that the strut is coupled to. The two degrees of freedom is obtained by utilizing one pivot joint and one hinge joint. The struts of the present invention include a threaded rod that rotates with respect to a telescopic tube. A function of the threaded rod being able to rotate with respect to the tube provides an additional degree of freedom. It also allows the struts to be attached and tightened directly to the rings. Overall, each strut will have two degrees of freedom at each end and one degree of freedom at the threaded rod level for a total of five degrees of freedom.

A second aspect of the present invention is with regard to coupling a strut attachment member to a body of a strut. The struts have a variable attachment point that will allow it to have at least two different attachment sites on the body of the strut. The attachment sites can either be at the middle of the strut body or at an end of the strut body. Coupling the strut attachment to the middle of the strut body provides a tight ring to ring distance when needed.

A third aspect of the present invention is a telescopic tube having markings on opposite sides of a slot about a length of the tube. These markings allow the tubes to display accurate lengths of the struts when the strut attachment is coupled to the strut body at its middle or at its end.

Another aspect of the present invention is an external fixation system comprising first and second ring members and first and second strut attachments members. The first strut attachment member is pivotably coupled at a first end to the first ring member and at a second end to a first end of an adjustable length strut. The second strut attachment member is pivotably coupled at a first end to the second ring member and at a second end to a length of the adjustable length strut.

In one embodiment of this aspect of the present invention, the first strut attachment member includes first and second pivot portions, the first pivot portion pivotably coupling the first strut attachment member to the first end of the adjustable length strut about a first axis and the second pivot portion pivotably coupling the first strut attachment member to the first end of the adjustable length strut about a second axis perpendicular to the first axis.

In another embodiment, the first end of the first strut attachment member has a bore adapted to receive a fastener for securing the first end of the first strut attachment member to at least one of a plurality of holes in the first ring.

In yet another embodiment, the first end of the first strut attachment member is located proximally to a top surface of the first ring when the first strut attachment member is coupled to the first ring.

In still yet another embodiment, the adjustable length strut comprises a rod member, a tube member and an actuation mechanism. The rod member extends between the first end and a second end of the adjustable length strut, the rod member including external threads. The tube member extends between the first and second ends of the adjustable length strut, the tube member including a hollow portion adapted to receive the rod member and an engagement feature adapted to engage the external threads of the rod member. The actuation mechanism rotatably fixed to the rod member, the actuation mechanism including a plurality of gear teeth extending radially outward of a longitudinal axis of the rod member.

In still yet another embodiment, the adjustable length strut further comprises a protrusion member coupled to an end portion of the rod member, the protrusion member extending substantially orthogonal to the longitudinal axis of the rod member, the protrusion member includes a collar portion substantially surrounding the end portion of the rod member, wherein the collar portion is freely rotatable with respect to the end portion of the rod member.

In still yet another embodiment, the tube member includes an elongate slot extending through inner and outer surfaces of the tube member, a portion of the protrusion member extends through a portion of the elongate slot, and wherein the tube member includes visual indicia on the outer surface thereof adjacent the slot.

Another aspect of the present invention is an external fixation system comprising a first ring member, a second ring member, a first strut attachment member pivotably coupled at a first end to the first ring member and at a second end proximate to a first end of an adjustable length strut, and a second strut attachment member pivotably coupled at a first end to the second ring member and at a second end to an outer surface of the adjustable length strut between the first end a second end of the adjustable length strut.

Another aspect of the present invention is an external fixation system comprising a first ring member, a second ring member, a first strut attachment member pivotably coupled at a first end to the first ring member and at a second end to a first end of an adjustable length strut, and a second strut attachment member pivotably coupled at a first end to the second ring member and at a second end to one of a plurality of positions about the length of the adjustable length strut between the first end and a second end of the adjustable length strut.

BRIEF DESCRIPTION OF THE DRAWINGS

A more complete appreciation of the subject matter of the present invention and the various advantages thereof can be realized by reference to the following detailed description in which reference is made to the accompanying drawings in which.

DETAILED DESCRIPTION

Figure 1:
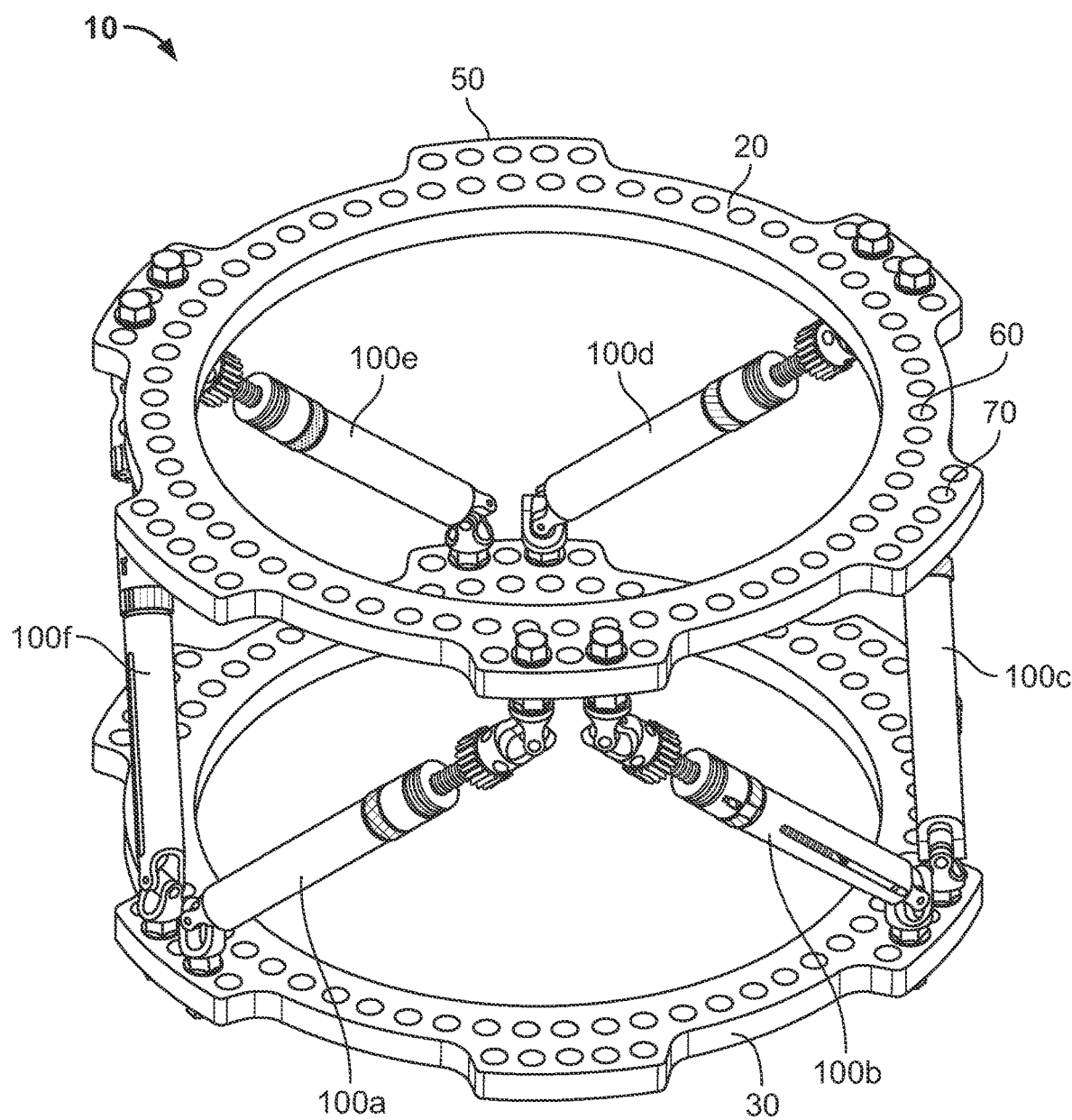
FIG. 1 is a perspective view of an external fixation system according to an embodiment of the disclosure.

FIG. 1 shows an external fixation frame 10 in an assembled condition according to one aspect of the disclosure. Generally, fixation frame 10 includes a first ring 20 and a second ring 30, with six telescopic struts 100a-f coupling the first ring 20 to the second ring 30. The first ring 20 may also be referred to as a proximal ring or a reference ring, while the second ring 30 may also be referred to as a distal ring or a moving ring. In the illustrated embodiment, each strut 100a-f includes a threaded portion that may thread into or out of a tube portion, for example by interaction with quick release mechanism 130, to decrease or increase the length, respectively, of the telescopic strut. Each end of each strut 100a-f may be coupled to the first ring 20 and second ring 30 via a joint mechanism, such as a ball joint, a constrained hinge joint, or a universal joint as illustrated. The use of universal joints on each end of the strut provides for six degrees of freedom of motion of the external fixation system 10. It should be understood that although the disclosure is generally described in the context of closed circular rings, the concepts described herein may apply with equal force to other types of rings, such as open rings and/or U-shaped rings.

In external fixation system 10, telescopic struts 100a-f are used to reduce fractures and correct deformities over time. Patients correct the deformities by prescribed adjustments of the struts 100a-f. The lengths of the struts 100a-f are adjusted over time to change the position and orientation of the two rings 20, 30 with respect to one another, which in turn repositions and reorients the bone fragments, with a goal of correcting the bone deformity. The adjustment of the external fixator 10 should strictly comply with the predetermined correction plan.

Rings 20 and 30 of external fixation system 10 may include a plurality of extension tabs 50. In the illustrated example, each ring 20 and 30 includes six extension tabs 50 spaced circumferentially around the perimeter of the respective rings, although more or fewer may be suitable depending on the particular components of the fixation system. In addition to what is described directly below, extension tabs 50 may help increase the cross-sectional area of rings 20, 30 and thus provide for increased stiffness of the rings.

With this configuration, each ring 20, 30 includes a first inner circumferential row of holes 60 and a second outer circumferential row of holes 70. As illustrated, the second outer circumferential row of holes 70 may be only positioned on the plurality of extension tabs 50 on the rings 20 and 30. It should be understood that although the second outer circumferential row of holes 70 is shown in FIG. 1 as being positioned solely on extension tabs 50, top ring 20 and/or bottom ring 30 may contain two complete rows of holes, for example with a completely circular (or nearly completely circular) geometry. The use of extension tabs 50, compared to two full circumferential rows of holes, may help reduce overall bulk of rings 20, 30 and also provide for intuitive strut placement for surgical personnel. The completely circular version of rings 20, 30 with two full (or nearly full) rows of circumferential holes may be particularly suited for relatively small diameter rings, although indentations or other features may be introduced to provide an intuitive interface for strut placement by surgical personnel. Further, in the illustrated embodiment, the first and second circumferential rows of holes 60 and 70 are positioned so that the first row of holes 60 does not align radially with the second row of holes 70. In other words, the first row of holes 60 has a staggered configuration with respect to the second row of holes 70. The additional hole options may also be utilized for connecting other components, such as fixation pins to couple the rings 20, 30 to the respective bone fragments. Still further, the staggered configuration of holes between the first and second rows 60, 70 may also help prevent interference between components attached to nearby holes, for example such as a strut 100a-f positioned in a first hole and a fixation pin or other fixation member attached to an adjacent or nearby second hole. For example, a relatively thin wire extending radially from one of the holes in the first circumferential row 60 may not radially interfere with a hole positioned in the second circumferential row 70 because of the radial staggering. It should be understood that the size of the tabs 50 may increase or decrease depending on the diameter of the rings 20 and 30, with greater diameter rings 20 and 30 having larger tabs 50 with more holes 70 compared to smaller diameter rings. For example, the illustrated tabs 50 include six holes 70, and a smaller ring may include smaller tabs with four holes each, for example.

Figure 2A:
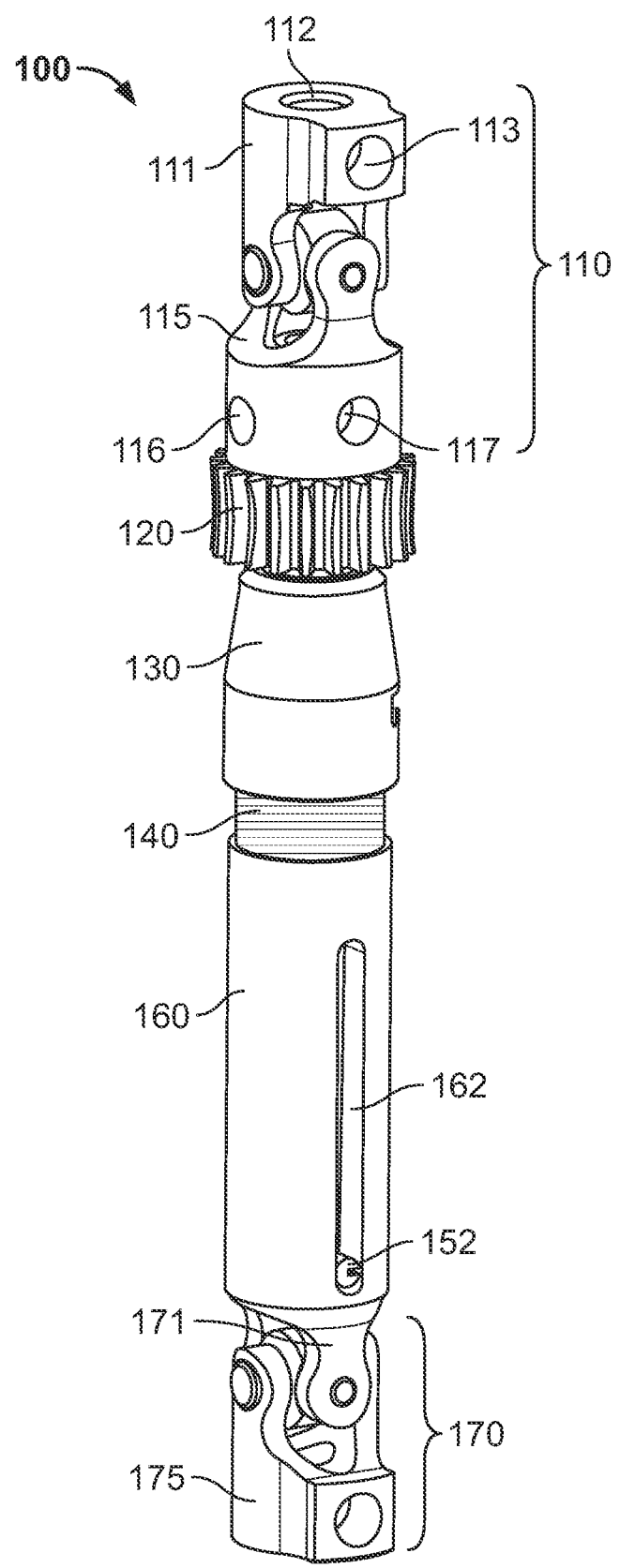
FIG. 2A is a perspective view of a strut of the external fixation system of FIG. 1.

FIG. 2A illustrates a perspective view of one telescopic strut 100 from the external fixation system 10 of FIG. 1. It should be understood that the components of struts 100a-f may be identical to one another, although some struts 100a-f may have different sizes than other struts 100a-f and may include different indicia, such as colors or markings for identification purposes, as described in greater detail below. For purposes of this disclosure, the term proximal refers to the top of the strut 100 in the orientation of FIG. 2A, and the term distal refers to the bottom of the strut 100 in the orientation of FIG. 2A. The proximal end portion of strut 100 may include a first joint 110, which is shown in this example as a universal joint. Joint 110 may include a proximal portion 111, which may include a first aperture 112 aligned substantially parallel with the longitudinal axis of strut 100 and a second aperture 113 aligned substantially transverse or orthogonal to the first aperture 112. The first aperture 112 may be configured to receive a fastener that passes through a hole in proximal ring 20 to secure the proximal portion 111 of joint 110 to proximal ring 20. The fastener may be connected so that the proximal portion 111 does not rotate relative to proximal ring 20. The second aperture 113 may be configured to receive a portion of a tool to prevent proximal portion 111 from rotating, for example while a fastener is being screwed into or otherwise inserted into first aperture 112. Joint 110 may also include a distal portion 115 with a first aperture 116 and a second aperture 117, the first and second apertures 116, 117 being aligned substantially transverse and/or orthogonal to one another and to the longitudinal axis of strut 100. First and second apertures 116, 117 may be used as attachment points for attaching additional components to strut 100 such as modular attachment piece 180 shown in FIG. 3 and further described in U.S. Ser. No. 15/181,614 titled "Gear Mechanisms for Fixation Frame Struts," the disclosure of which is incorporated by reference herein in its entirety.

Still referring to FIG. 2A, strut 100 may include additional components including an actuation mechanism 120, a quick-release mechanism 130, a strut identifier 140, a threaded rod 150 (not visible in FIG. 2A), a tube 160, and a second joint 170. As noted above, the effective length of strut 100, which may be thought of as the distance between the proximal end and distal end of strut 100, may be adjusted by threading the threaded rod 150 of strut 100 into or out of tube 160 through interaction with quick-release mechanism 130.

Figure 2B:
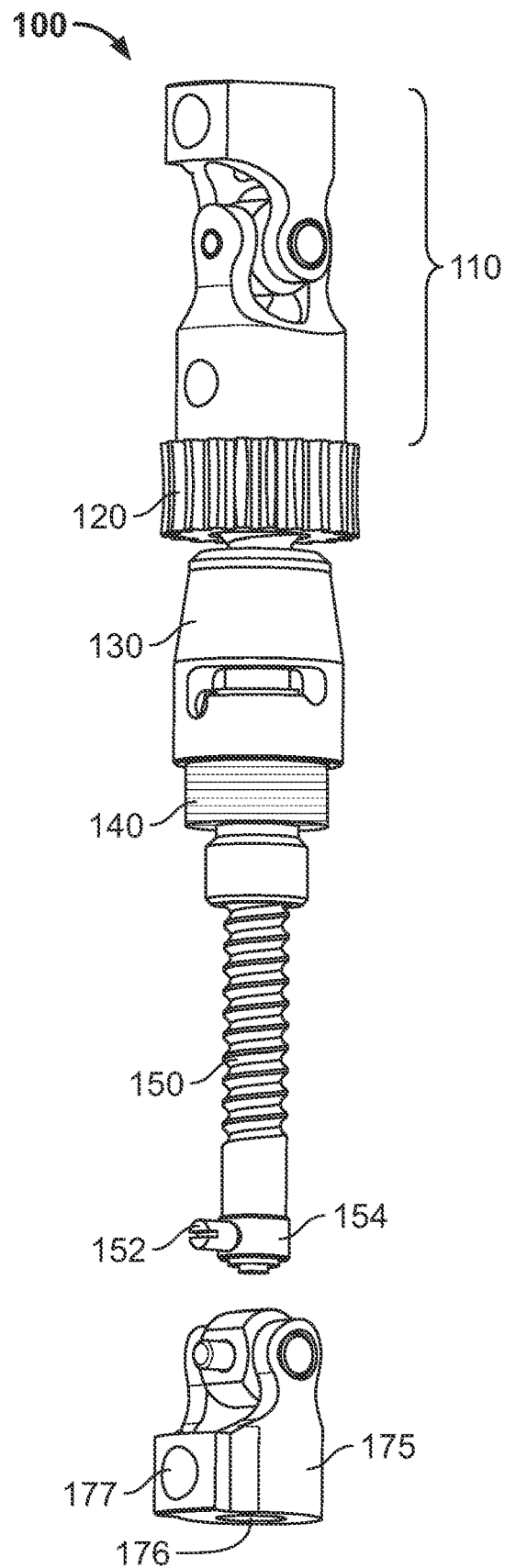
FIGS. 2B-C are perspective views of the strut of FIG. 2A with certain components omitted.
Figure 2C:
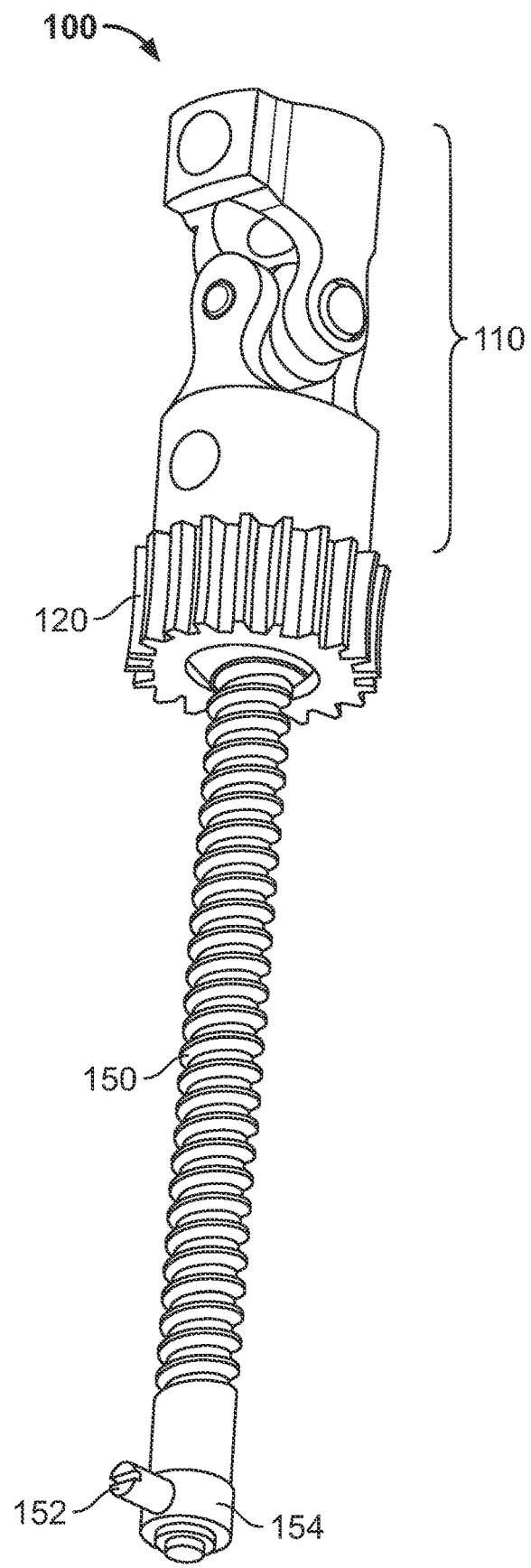

FIG. 2B illustrates strut 100 with tube 160 omitted for clarify of illustration. FIG. 2C illustrates strut 100 with tube 160, as well as quick-release mechanism 130, strut identified 140, and second joint 170 omitted for clarity of illustration.

Figure 2D:
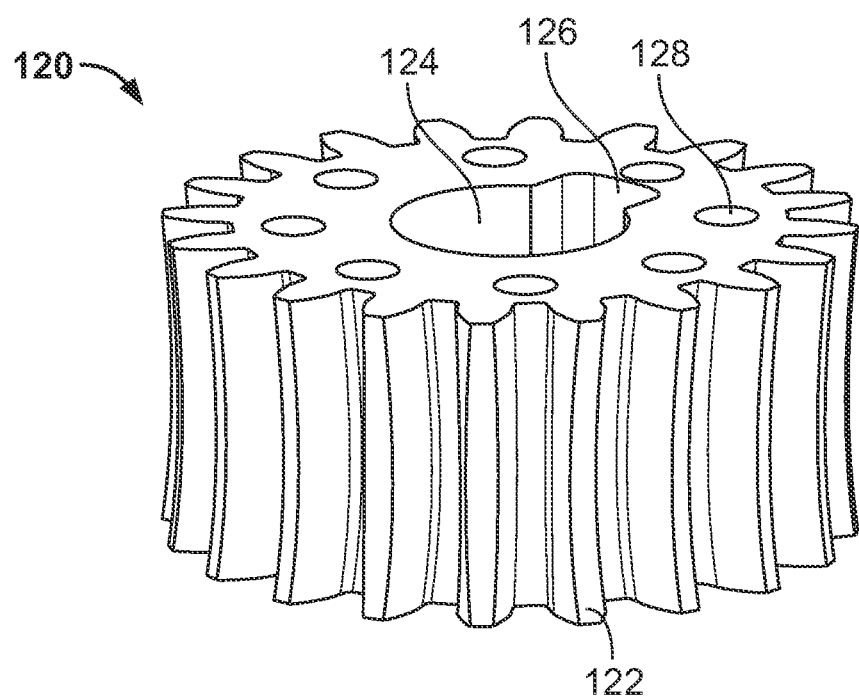
FIG. 2D is a perspective view of an actuation mechanism of the strut of FIG. 2A.

Actuation mechanism 120 is shown isolated in FIG. 2D. Actuation mechanism 120 may be generally a short, cylindrical component with a plurality of ridges or gear teeth 122 extending around the circumference of actuation mechanism 120. The actuation mechanism 120 may be rotatably coupled to threaded rod 150 so that rotation of actuation mechanism 120 causes a corresponding rotation of threaded rod 150. For example, actuation mechanism 120 may have a channel 124 extending therethrough, with an extension 126 in channel 124 that mates with a corresponding extension in threaded rod 150, so that rotation of actuation mechanism 120 causes rotation of threaded rod 150. It should be understood that the threaded rod 150 may rotate with respect to the first joint 110, the first joint 110 and second joint 170 being rotatably fixed to rings 20 and 30, respectively. The proximal surface of actuation mechanism may include a plurality of divots or grooves 128 sized to accept a ball which is biased into the groove via a spring. The spring may have a first end in contact with a distal surface of first joint 110, with a distal end pressing a ball into the proximal surface of actuation mechanism 120. With this configuration, an amount of force is required to rotate actuation mechanism 120 to overcome the force of the spring pushing the ball into the divot 128. As rotation of actuation mechanism 120 continues, the ball will eventually be positioned adjacent an adjacent groove 128. As rotation continues further, the spring will force the ball into the next groove 128 when the ball is aligned with the groove 128, causing a tactile and/or audible click. Each "click" may correspond to a particular axial change in length so that a user knows, for example, that four "clicks" correspond to 1 mm of length adjustment. Similar "clicking mechanisms" are described in greater detail in U.S. Pat. No. 8,834,467, the contents of which are hereby incorporated by reference herein.

Referring now to FIGS. 2A-B, quick-release mechanism 130 may generally take the form of an outer housing that surrounds a portion of threaded rod 150. Quick-release mechanism 130 may have a disengaged state and an engaged state. In the disengaged state, threaded rod 150 may be capable of moving into or out of tube 160 without rotation of the threaded rod 150, for quick adjustments of the length of strut 100, which may be useful for example while initially assembling the fixation frame 10. Rotating the quick-release mechanism 130 may transition the quick-release mechanism 130 into the engaged state, in which threated rod 150 may only move axially into or out of tube 160 via rotation of the threaded rod 150. The mechanism for keeping the quick-release mechanism 130 in the engaged state may include a ball or other feature that is forced between adjacent threads of threaded rod 150 so that axial translation of the threaded rod 150 is only possible via rotation, so that rotation of threaded rod 150 axially moves the threaded rod 150 into the tube 160, without requiring the tube 160 to have internal threading. It should be understood that the quick-release mechanism 130 is not a necessary component of strut 100, and may be omitted from strut 100 if desired. If quick-release mechanism 130 is omitted, it may be preferably to include internal threads on tube 160 to correspond to external threads on threaded rod 150. Further details of quick-release mechanisms have been described elsewhere, including, for example, in U.S. Pat. No. 9,101,398, the contents of which are hereby incorporated by reference herein.

A strut identifier 140 may be coupled to strut 100 at any desired location, for example between the quick-release mechanism 130 and the tube 160. Strut identifier 140 may take the form of a clip or any other suitable shape that can be quickly and securely clipped onto the strut 100 and removed from strut 100. For example, in the illustrated embodiment, strut identifier 140 is a "C"-shaped clip that is flexible enough to open for easy connection to strut 100, but rigid enough that the strut identifier 140 is not easily removed from strut 100 without intentional application of force. Strut identifier 140 may have a color or other identifier such as a number, letter, or shape pattern. Each strut 100a-f may have a strut identifier 140 that is structurally similar or identical, but that each has easily distinguishable indicia, such as different colors, different numbers, etc. Strut identifiers 140 may be used so that each strut 100a-f is easily distinguished from one another, and so that other matching indicia may be provided on other components, described in greater detail below, that may be added onto struts 100a-f so that each additional component may be easily matched with the correct corresponding strut 100a-f. Strut identifier 140 may also function to prevent unintentional disengagement of the quick release mechanism 130.

Referring again to FIG. 2A, tube 160 may be a generally hollow cylindrical tube configured to allow threaded rod 150 to move axially into or out of tube 160 to decrease or increase the effective length of strut 100, respectively. As noted above, such axial movement may be produced by rotation of threaded rod 150 when the quick release mechanism 130 is in the engaged position, so that the threads of the threaded rod 150 engage the ball or other mechanism within the quick release mechanism 130. If omitting the quick release mechanism 130, the tube 160 may include internal threads that mate directly with the external threads of the threaded rod 150. A slot 162 may extend along part of the length of the tube 160, the slot 162 opening the hollow inside of the tube 160 to the exterior of the tube at both inner and outer sides such that there are two slots 162 at least one of which will be visible to the user depending on the orientation of tube 160 during use. The slot 162 may have a width slightly larger than the width of button 152. Referring now to FIGS. 2B-C, the distal end of threaded rod 150 may include a button 152 coupled to a collar 154, the collar 154 surrounding the distal end of threaded rod 150. Collar 154 may be positioned with a groove at the distal end of threaded rod 150 so that collar 154 may rotate freely around the axis of the strut 100 while being axially fixed with respect to the threaded of 150. Referring again to FIG. 2A, as threaded rod 150 is threaded into or out of tube 160, button 152 travels up or down the slot 162 of the tube 160, which is possible because button 152 and collar 154 are free to rotate with respect to threaded rod 150. Tube 160 may include indicia, such as hash marks and/or measurements, on or adjacent to slot 162. The position of button 152 along slot 162 may correspond to the effective length of the strut 100, so that a user can easily determine the effective length of the strut based on the indicia adjacent to the position of button 152 at any particular time.

Referring still to FIG. 2A, the distal end of tube 160 may include two extensions that form a proximal portion 171 of second joint 170. Second joint 170 may include a distal portion 175 that, together with proximal portion 171 and an internal mechanism form a universal joint similar to first joint 110. Distal portion 175 may include a first aperture 176 that is aligned substantially parallel with strut 100. Aperture 176 may be adapted to receive a fastener therein to couple second joint 170 to distal ring 30. The fastener may be a screw or other type of fastener, and may be adapted to tightly couple the second joint 170 to the distal ring 30 so that the second joint 170 does not rotate with respect to distal ring 30. With this configuration, the slot 162 of tube 160 may be positioned outward (away from the center of proximal and distal rings 20, 30) so that the position of button 152 with respect to indicia on tube 160 may be easily read at all times. The distal portion 175 of second joint 170 may include a second aperture 177 aligned substantially orthogonal to first aperture 176 and adapted to receive a tool to keep second joint 170 from rotating, for example while a fastener is screwed into first aperture 176. This may help ensure, for example, the slot 162 of tube 160 is facing away from the center of the rings 20, 30 as the strut 100 is tightened to the rings 20, 30. It should also be understood that in some prior art devices, rotational freedom of the strut was provided by loosely coupling the joint(s) to the ring(s) so that the joints themselves could swivel. In the present disclosure, the rotational degree of freedom is provided by the ability of threaded rod 150 to rotate, while the tight attachment of the first joint 110 and second joint 170 to the first ring 20 and second ring 30 provides for a more stable connection.

Figure 3:
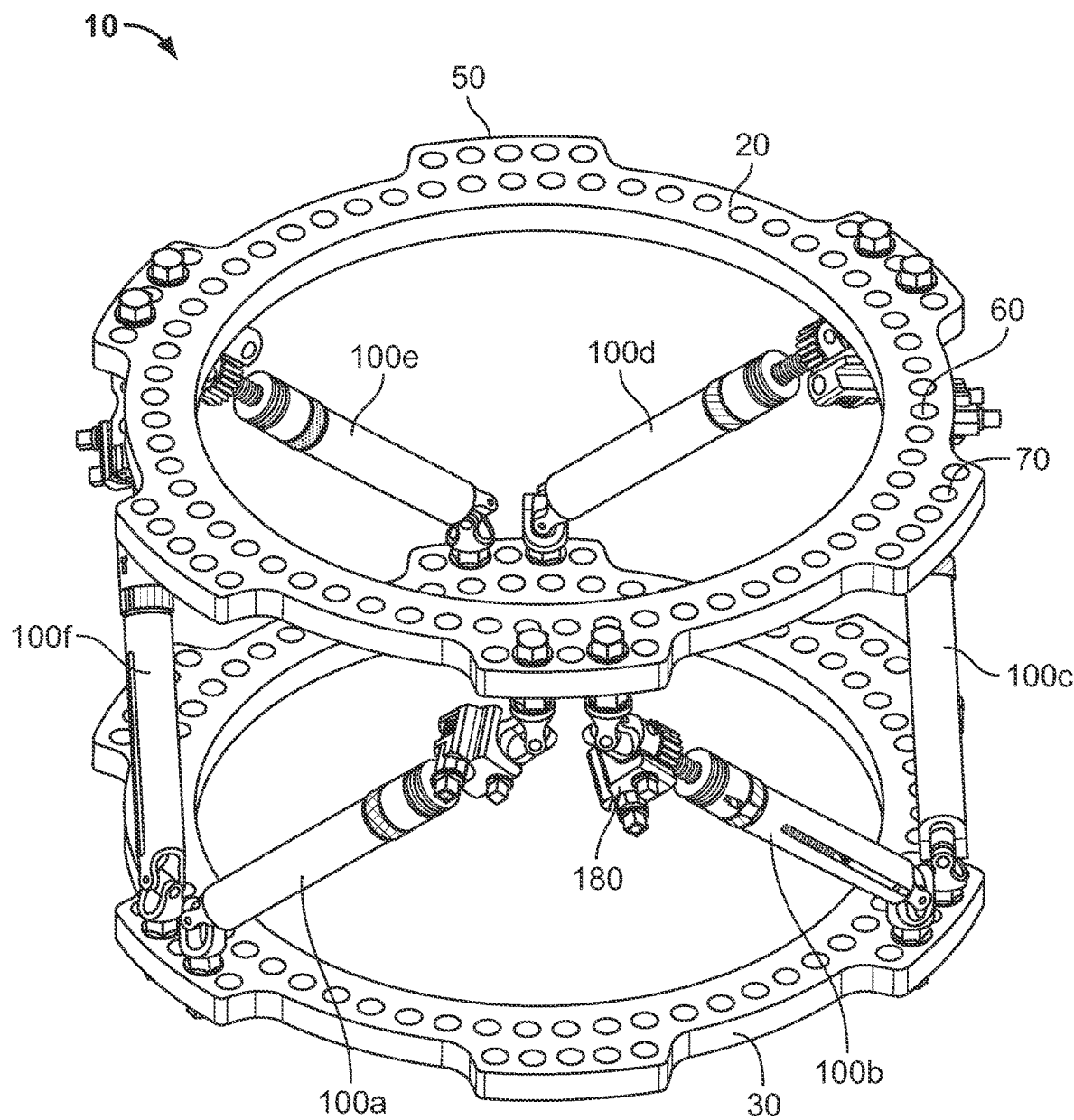
FIG. 3 is a perspective view of the external fixation system of FIG. 1 with modular attachment members coupled to the struts.

It should be understood that strut 100 as described above may be designed for manual actuation, for example by a user gripping the actuation mechanism 120 with his hand and manually rotating the actuation mechanism 120. However, it should be understood that a tool may be used, either directly on actuation mechanism 120 or with intervening components, to adjust the length of strut 100. For example, FIG. 3 illustrates the external fixation system 10 of FIG. 1 with completely identical components, with the exception that each strut 100a-f includes a modular attachment piece 180 coupled to a corresponding strut 100a-f. As is described in U.S. Ser. No. 15/181,614 incorporated by reference herein, modular attachment piece 180 provides a variety of benefits, including a simple way to allow a user to adjust struts 100a-f with a tool rather than through manual adjustment.

Figure 4:
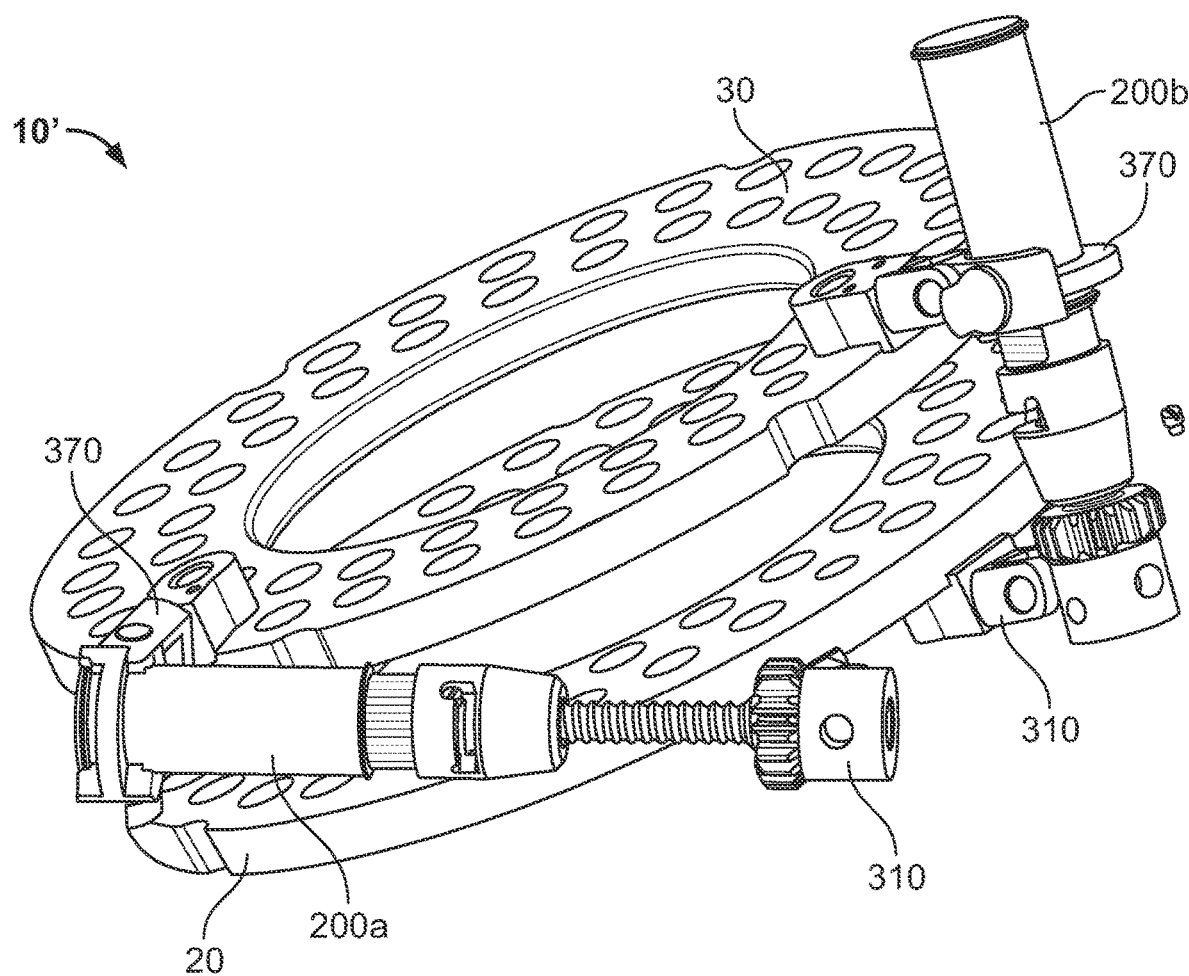
FIG. 4 is a perspective view of an external fixation system according to an embodiment of the disclosure showing strut attachment members of the present invention coupling first and second struts to respective first and second rings.
Figure 5A:
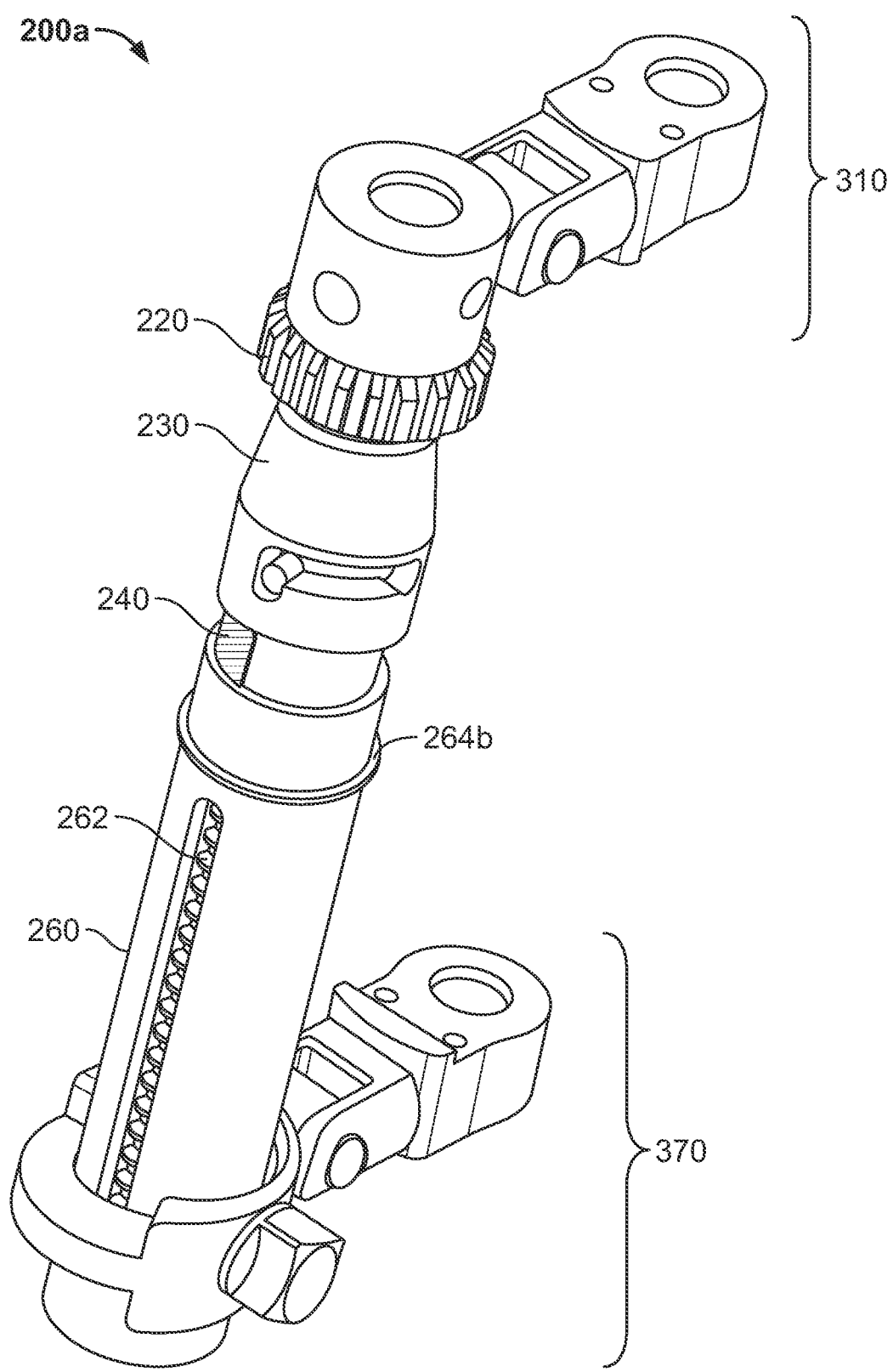
FIG. 5A is a perspective view of a strut with strut attachment members coupled to the strut in a first configuration.
Figure 5B:
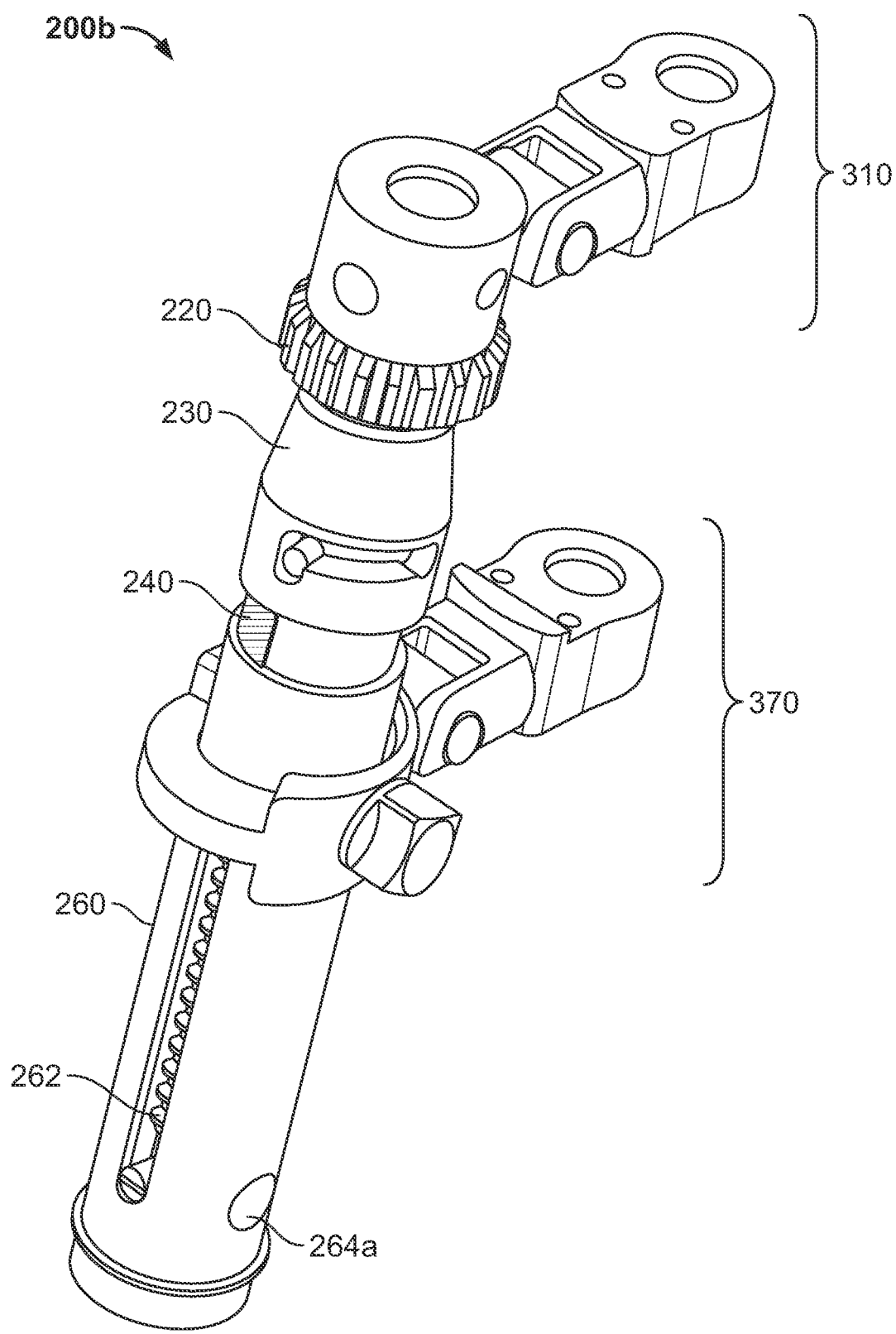
FIG. 5B is a perspective view of a strut with strut attachment members coupled to the strut in a second configuration.

FIG. 4 is a perspective view of an external fixation system 10' according to another embodiment of the disclosure showing strut attachment members 310, 370 of the present invention each coupling first and second struts 200a, 200b to respective first and second rings 20, 30. FIG. 5A is a perspective view of first strut 200a with strut attachment members 310, 370 coupled to the strut in a first configuration while FIG. 5B is a perspective view of second strut 200b with strut attachment members 310, 370 coupled to the strut in a second configuration. In reference to first and second struts 200a, 200b, each may include additional components including an actuation mechanism 220, a quick-release mechanism 230, a strut identifier 240, a threaded rod 250 (not visible in FIGS. 5A, 5B), a tube 260 and a slot 262 extending along the length of the tube 260. As noted above, the effective length of struts 200a, 200b, which may be thought of as the distance between the proximal end and distal end of strut 200a, 200b, may be adjusted by threading the threaded rod 250 of each strut 200a, 200b into or out of tube 260 through interaction with quick-release mechanism 230.

In reference to FIGS. 5A and 5B, the proximal end portion of each strut 200a, 200b include a first strut attachment member 310 instead of first joint 110 shown, for example, in FIG. 2a. Each strut 200a, 200b also include a translatable second strut attachment member 370 instead of fixed location second joint 170 as also shown, for example, in FIG. 2a.

Strut attachment member 310 is pivotably coupled at a first end thereof to a first ring member 20, 30 and at a second end thereof to a first end of adjustable length strut 200a, 200b. Strut attachment member 370 is pivotably coupled at a first end thereof to a second ring member 20, 30 and at a second end thereof to a length of the adjustable length strut 200a, 200b. The struts of the present invention has at least two modes of operation, such as "Long mode" in reference to strut 200a and "Short Mode" in reference to strut 200b.

When the surgical indication require a very tight right to ring distance, strut attachment member 310 is fixed to a proximal ring, for example, while strut attachment member 370 is attached to a middle portion of the strut, followed by attaching that level to the distal ring, for example. At this point, the struts will be either in the minimum distance between the joints or somewhere between the minimum and the maximum distance of the joints. During correction when the strut is extended to the maximum length, which is represented by the indicator pins touching the top of the slot of the tube, the strut change out device is applied. The strut change out device holds the two rings tight with respect to each other. At this point bottom joint that is attached to the middle of the strut is unlocked followed by unlocking the quick release. The whole tube is moved up and spun 180° so that the slot on the opposite direction that used to face inwards now faces outwards. The bottom joint is now locked at the bottom end of the strut, followed by locking the quick release. This will result in the "Long Mode" of strut operation. This will allow the same strut to get another full length of telescoping to allow maximum distraction just with one strut.

Figure 6A:
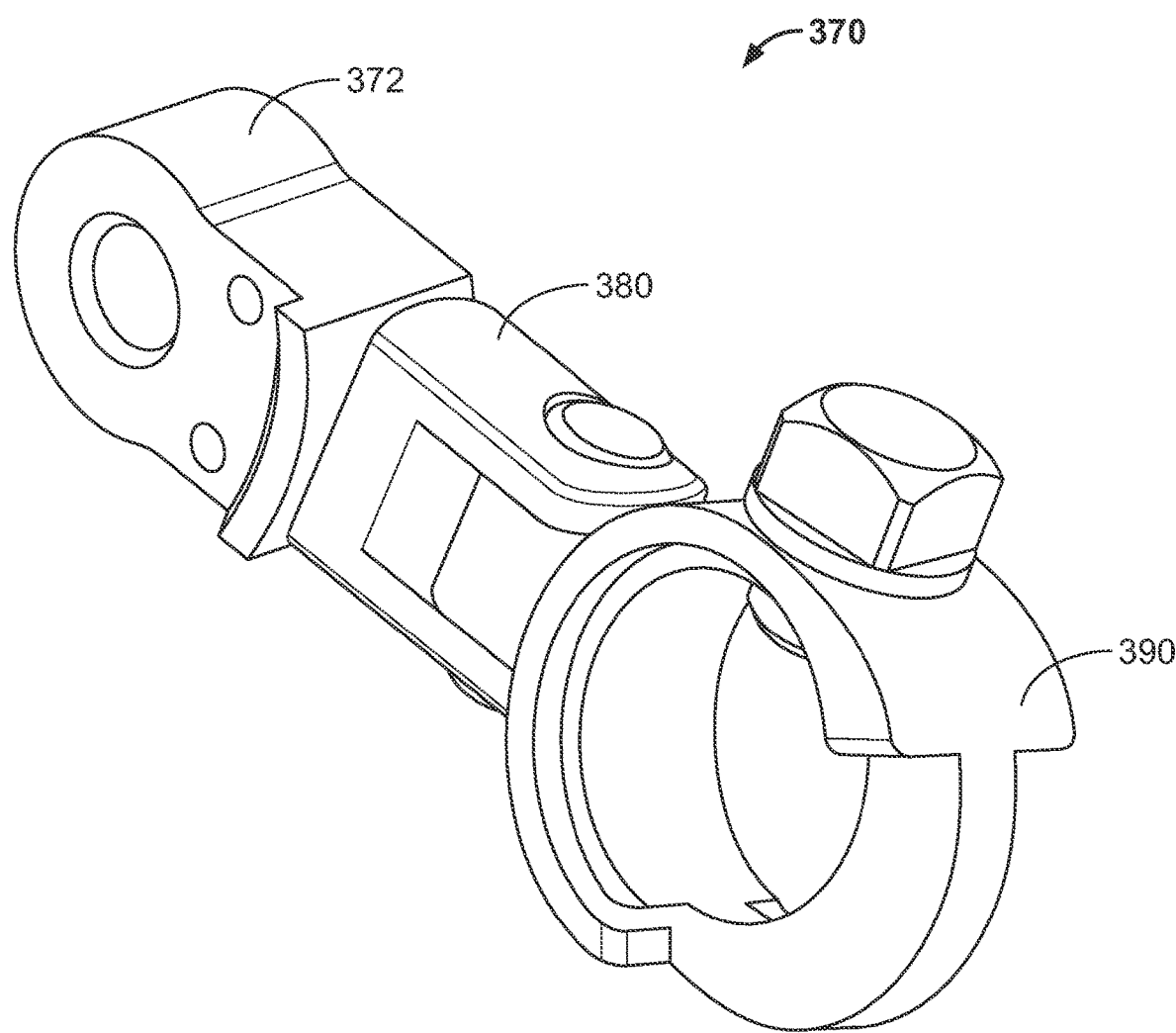
FIG. 6A is a perspective view of a strut attachment member of the present invention that is configured to be coupled about the body of a strut.
Figure 6B:
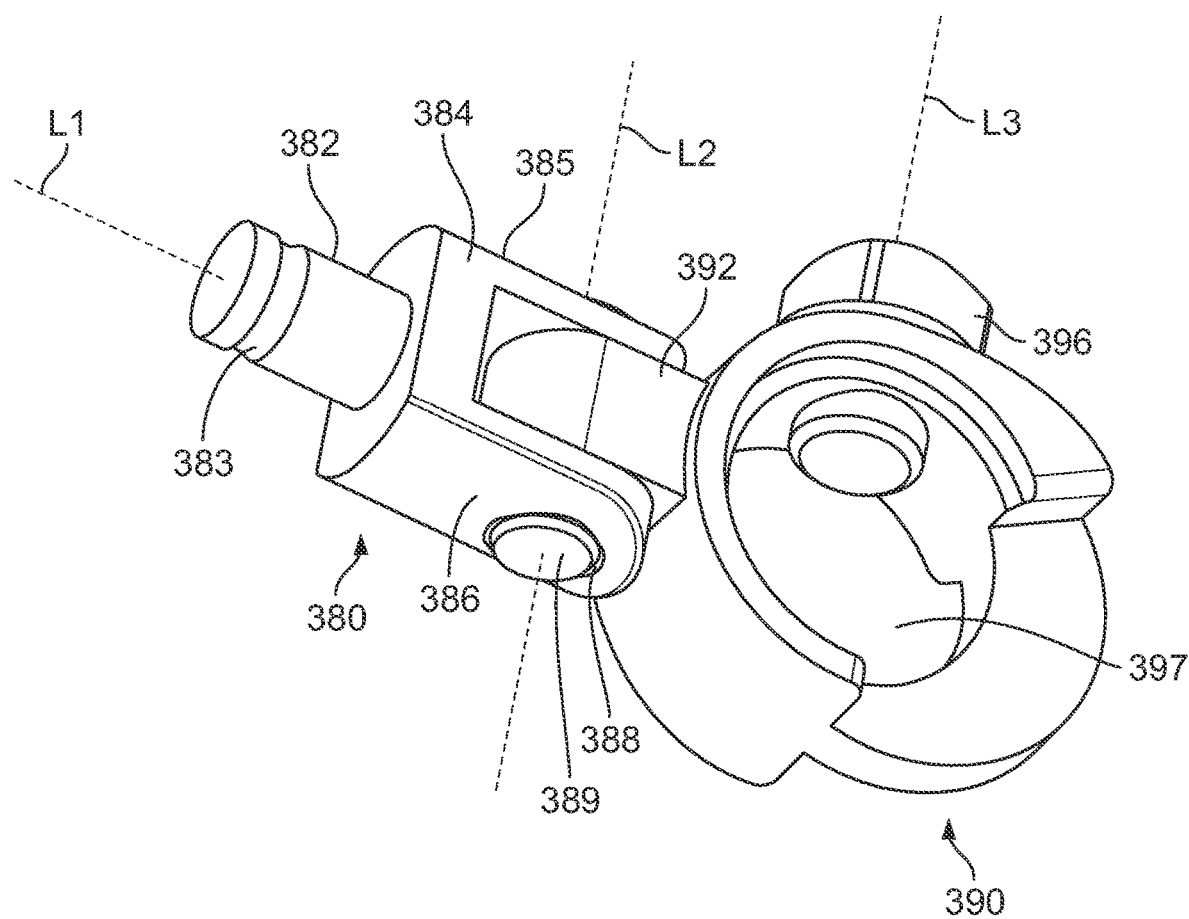
FIG. 6B is a partially exploded perspective view of a ring connector portion separated from the intermediate and coupling portions of the strut attachment member shown in FIG. 6A.
Figure 6C:
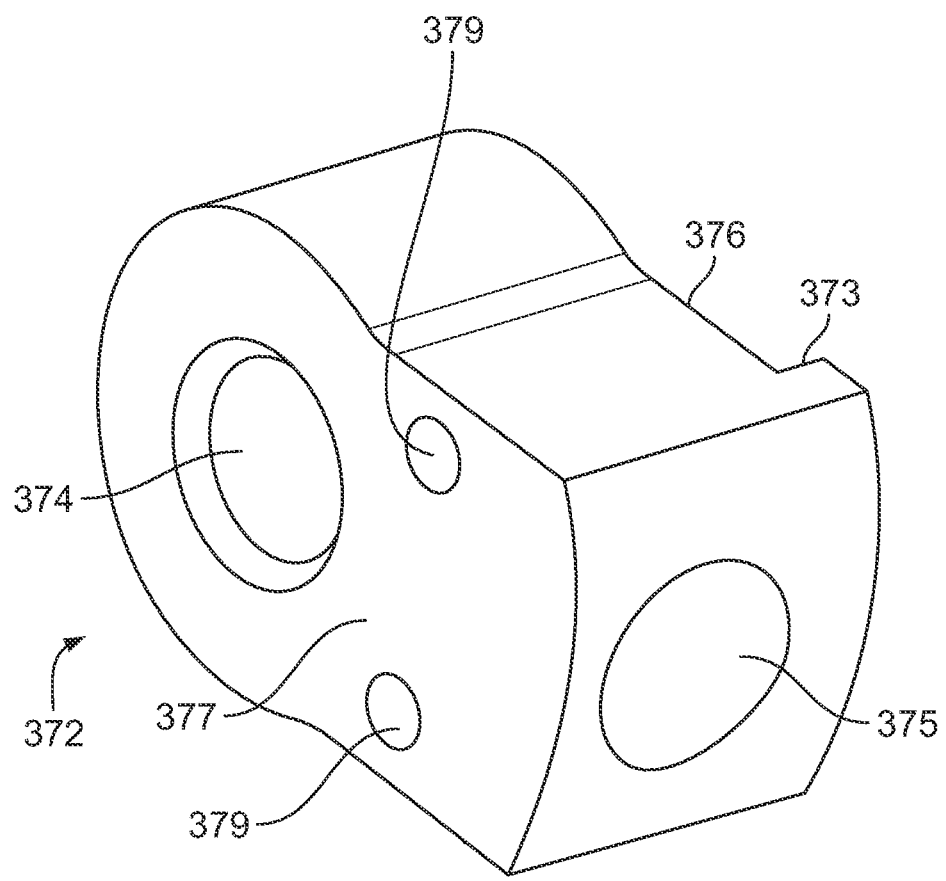
FIG. 6C is a perspective view of the ring connector portion shown in FIG. 6A.

FIG. 6A is a perspective view of strut attachment member 370 of the present invention that is configured to be coupled about the tube or body 260 of struts 200a, 200b. Strut attachment member 370 includes a ring connector portion 372, an intermediate portion 380 and a coupling portion 390. Strut attachment member 370 allows for two degrees of freedom between the strut and a respective ring that the strut is coupled to. The two degrees of freedom is obtained by utilizing one pivot joint and one hinge joint. FIG. 6B shows ring intermediate portion 380 and coupling portion 390 of strut attachment member 370 without ring connected portion 372. As shown in FIG. 6C, ring connector portion 372 includes a corner ledge portion 373 for receipt of a corresponding corner of rings 20, 30 to position ring connector portion 372 and to prevent rotation thereof prior to fixing ring connector portion 372 to rings 20, 30. A fastener (not shown) is received within aperture 374 and a hole of rings 20, 30 in order to secure ring connector portion 372 to rings 20, 30. Ring connector portion 372 includes first and second lateral bores 379 for receipt of pins (not shown) in order to secure post 382 of intermediate portion 380 within transverse aperture 375 of ring connector portion 372 defining a pivot joint.

As shown in FIG. 6B, post 382 includes a circular recess 383 therein, the pins being received in a portion of the recess after post 382 is fully received within transverse aperture 375 of ring connector portion 372 in order to secure post 382 of intermediate portion 380 within transverse aperture 375 while allowing intermediate portion 370 to pivot or rotate about a longitudinal axis L1 with respect to ring connector portion 372. Ring connector portion 372 further includes an inner surface 376 and an outer surface 377. The inner surface 376 is configured to lie adjacent a planar top or bottom surface of rings 20, 30 when ring connector portion 372 is coupled to rings 20, 30. Intermediate portion 380 further includes a u-shaped portion 384 extending from secure post 382. The u-shaped portion 384 includes first and second legs 385, 386 having apertures 388. A pivot pin 389 is received within apertures 388 of first and second legs as well as an aperture (not shown) in an extension 392 of coupling portion 390. Pivot pin 389 forms a hinge joint between intermediate portion 380 and coupling portion 390 and allows intermediate portion 380 to pivot with respect to coupling portion 390 about a longitudinal axis L2 perpendicular to L1. Coupling portion 390 further includes a bore 394 for receipt of tube 260 and a movable pin 396 received within an aperture 397 of coupling portion 390. Movable pin 396 is moved about an axis L3 in order to position coupling portion 390 within a corresponding feature 264a, 264b of tube 260 in order to position strut attachment 370 in either a first position as shown for example in FIG. 5A or a second configuration as shown for example in FIG. 5B.

Figure 7:
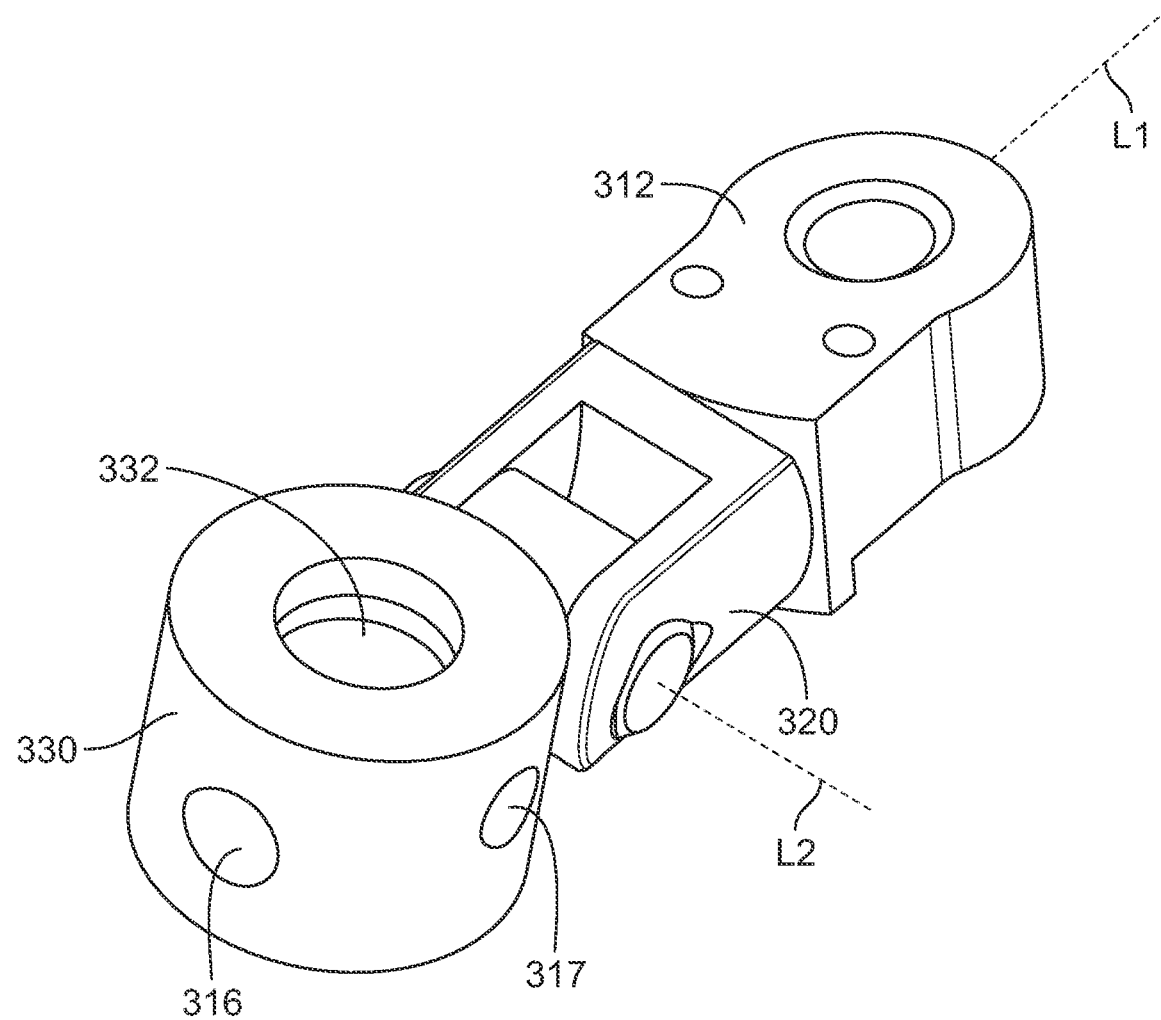
FIG. 7 is a perspective view of a strut attachment member of the present invention that is configured to be coupled at an end of a strut.

FIG. 7 is a perspective view of strut attachment member 310 of the present invention that is configured to be coupled at an end of a strut. Strut attachment member 310 includes a ring connector portion 312 (similar to ring connector portion 372), an intermediate portion 320 (similar to ring connector portion 380) and a coupling portion 330. Coupling portion 300 includes a longitudinal bore 332 for receipt of a post 222 in order to couple coupling portion 300 to an end of the strut. Coupling portion 300 further includes a first aperture 316 and a second aperture 317, the first and second apertures 316, 317 being aligned substantially transverse and/or orthogonal to one another and to the longitudinal axis of struts 200a, 200b. First and second apertures 316, 317 may be used as attachment points for attaching additional components to strut 200a, 200b such as modular attachment piece 180.

Although the invention herein has been described with reference to particular embodiments, it is to be understood that these embodiments are merely illustrative of the principles and applications of the present invention. For example, features described in relation to one particular embodiment may be combined with features of other embodiments described herein. It is therefore to be understood that numerous modifications may be made to the illustrative embodiments and that other arrangements may be devised without departing from the spirit and scope of the present invention as defined by the appended claims.

The invention claimed is:
1. An external fixation system comprising:
a first ring member defining an outer proximal surface, an opposite inner distal surface, and an outer circumferential extent;
a second ring member defining an outer distal surface, an opposite inner proximal surface, and an outer circumferential extent, the inner proximal surface of the second ring member facing the inner distal surface of the first ring member in an assembled condition of the external fixation system;
a first strut attachment member having a first portion coupled to the outer proximal surface of the first ring member and a second portion coupled to a first end of an adjustable length strut in the assembled condition of the external fixation system, and a third portion pivotably coupled to the first and second portions, the third portion having a pivot portion pivotably coupling the first and third portions, the first portion including a bore configured to receive a fastener, the bore extending along an axis extending from the outer proximal surface to the inner distal surface of the first ring member, and
a second strut attachment member having a first portion coupled to the outer distal surface of the second ring member and a second portion coupled to a length of the adjustable length strut in the assembled condition of the external fixation system, and a third portion pivotably coupled to the first and second portions,
wherein, in the assembled condition of the external fixation system, (i) the second portion of the first strut attachment member is positioned radially outward of the outer circumferential extent of the first ring member so that the first end of the adjustable length strut is positioned radially outward of the outer circumferential extent of the first ring member, and (ii) the second portion of the second strut attachment member is positioned radially outward of the outer circumferential extent of the second ring member so that the length of the adjustable length strut is positioned radially outward of the outer circumferential extent of the second ring member,
wherein the adjustable length strut comprises:
a rod member extending between the first end and a second end of the adjustable length strut, the rod member including external threads;
a tube member extending between the first and second ends of the adjustable length strut, the tube member including a hollow portion adapted to receive the rod member and an engagement feature adapted to engage the external threads of the rod member; and
an actuation mechanism rotatably fixed to the rod member, the actuation mechanism including a plurality of gear teeth extending radially outward of a longitudinal axis of the rod member,
wherein the adjustable length strut further comprises a protrusion member coupled to an end portion of the rod member, the protrusion member extending substantially orthogonal to the longitudinal axis of the rod member, the protrusion member includes a collar portion substantially surrounding the end portion of the rod member, wherein the collar portion is freely rotatable with respect to the end portion of the rod member,
wherein the tube member includes an elongate slot extending through inner and outer surfaces of the tube member, a portion of the protrusion member extends through a portion of the elongate slot, and wherein the tube member includes visual indicia on the outer surface thereof adjacent the slot.

2. The external fixation system of claim 1, wherein the first strut attachment member includes a pin, the pin pivotably coupling the second and third portions of the first strut attachment member.

3. The external fixation system of claim 1, wherein the fastener is configured to secure the first portion of the first strut attachment member to at least one of a plurality of holes in the first ring member.

4. The external fixation system of claim 1, wherein, in the assembled condition of the external fixation system, the first portion of the second strut attachment member is coupled to the outer distal surface of the second ring member.

5. An external fixation system comprising:
a first ring member defining an outer proximal surface, an opposite inner distal surface, and an outer circumferential extent;
a second ring member defining an outer distal surface, an opposite inner proximal surface, and an outer circumferential extent, the inner proximal surface of the second ring member facing the inner distal surface of the first ring member in an assembled condition of the external fixation system;
a first strut attachment member having a first portion coupled to the first ring member and a second portion coupled proximate to a first end of an adjustable length strut in the assembled condition of the external fixation system, and a third portion pivotably coupled to the first and second portions, the third portion having a pivot portion pivotably coupling the first and third portions; and
a second strut attachment member having a first portion coupled to the outer distal surface of the second ring member and a second portion coupled to a selected location on an outer surface of the adjustable length strut between the first end and a second end of the adjustable length strut in the assembled condition of the external fixation system, and a third portion pivotably coupled to the first and second portions,
wherein, in the assembled condition of the external fixation system, (i) the second portion of the first strut attachment member is positioned radially outward of the outer circumferential extent of the first ring member so that the first end of the adjustable length strut is positioned radially outward of the outer circumferential extent of the first ring member, and (ii) the second portion of the second strut attachment member is positioned radially outward of the outer circumferential extent of the second ring member so that the selected location of the adjustable length strut is positioned radially outward of the outer circumferential extent of the second ring member,
wherein the adjustable length strut comprises:
a rod member extending between the first and second ends of the adjustable length strut, the rod member including external threads;
a tube member extending between the first and second ends of the adjustable length strut, the tube member including a hollow portion adapted to receive the rod member and an engagement feature adapted to engage the external threads of the rod member; and
an actuation mechanism rotatably fixed to the rod member, the actuation mechanism including a plurality of gear teeth extending radially outward of a longitudinal axis of the rod member, wherein the adjustable length strut further comprises a protrusion member coupled to an end portion of the rod member, the protrusion member extending substantially orthogonal to the longitudinal axis of the rod member, the protrusion member includes a collar portion substantially surrounding the end portion of the rod member, wherein the collar portion is freely rotatable with respect to the end portion of the rod member, wherein the tube member includes an elongate slot extending through inner and outer surfaces of the tube member, a portion of the protrusion member extends through a portion of the elongate slot, and wherein the tube member includes visual indicia on the outer surface thereof adjacent the slot.

6. The external fixation system of claim 5, wherein the first strut attachment member includes a pin, the pin pivotably coupling the second and third portions of the first strut attachment member.

7. The external fixation system of claim 5, wherein the first portion of the second strut attachment member has a bore adapted to receive a fastener for securing the first portion of the second strut attachment member to at least one of a plurality of holes in the second ring member.

8. The external fixation system of claim 5, wherein the first portion of the first strut attachment member is coupled to the outer proximal surface of the first ring member in the assembled condition of the external fixation system.

9. An external fixation system comprising:
a first ring member defining an outer proximal surface, an opposite inner distal surface, and an outer circumferential extent;
a second ring member defining an outer distal surface, an opposite inner proximal surface, and an outer circumferential extent, the inner proximal surface of the second ring member facing the inner distal surface of the first ring member in an assembled condition of the external fixation system;
a first strut attachment member having a first portion coupled to the outer proximal surface of the first ring member and a second portion coupled to a first end of an adjustable length strut in the assembled condition of the external fixation system, and a third portion pivotably coupled to the first and second portions, the third portion having a pivot portion pivotably coupling the first and third portions; and
a second strut attachment member having a first portion coupled to the outer distal surface of the second ring member and a second portion coupled to one of a plurality of positions about the length of the adjustable length strut between the first end and a second end of the adjustable length strut in the assembled condition of the external fixation system, and a third portion pivotably coupled to the first and second portions, wherein, in the assembled condition of the external fixation system, (i) the second portion of the first strut attachment member is positioned radially outward of the outer circumferential extent of the first ring member so that the first end of the adjustable length strut is positioned radially outward of the outer circumferential extent of the first ring member, and (ii) the second portion of the second strut attachment member is positioned radially outward of the outer circumferential extent of the second ring member so that the one of the plurality of positions about the length of the adjustable length strut is positioned radially outward of the outer circumferential extent of the second ring member, wherein the adjustable length strut comprises:
a rod member extending between the first and second ends of the adjustable length strut, the rod member including external threads;
a tube member extending between the first and second ends of the adjustable length strut, the tube member including a hollow portion adapted to receive the rod member and an engagement feature adapted to engage the external threads of the rod member; and
an actuation mechanism rotatably fixed to the rod member, the actuation mechanism including a plurality of gear teeth extending radially outward of a longitudinal axis of the rod member.

10. The external fixation system of claim 9, wherein the first strut attachment member includes a pin, the pin pivotably coupling the second and third portions of the first strut attachment member.

11. The external fixation system of claim 9, wherein the first portion of the first strut attachment member has a bore adapted to receive a fastener for securing the first portion of the first strut attachment member to at least one of a plurality of holes in the first ring member.

12. The external fixation system of claim 9, wherein the first portion of the first strut attachment member is located proximally to a top surface of the first ring when the first strut attachment member is coupled to the first ring member.

13. The external fixation system of claim 9, wherein the adjustable length strut further comprises a protrusion member coupled to an end portion of the rod member, the protrusion member extending substantially orthogonal to the longitudinal axis of the rod member, the protrusion member includes a collar portion substantially surrounding the end portion of the rod member, wherein the collar portion is freely rotatable with respect to the end portion of the rod member.

* * * * *